US012412669B1

(12) United States Patent
Jackson et al.

(10) Patent No.: US 12,412,669 B1
(45) Date of Patent: Sep. 9, 2025

(54) PREDICTIVE MODELING FOR ENHANCED DECISION MAKING

(71) Applicant: C/HCA, INC., Nashville, TN (US)

(72) Inventors: Edmund Jackson, Nashville, TN (US); Martin Tobias, Mountain View, CA (US); Cody Hall, Nashville, TN (US); Nan Chen, Brentwood, TN (US); Betty A. Chodkowski, Nashville, TN (US)

(73) Assignee: C/HCA, Inc., Nashville, TN (US)

( * ) Notice: Subject to any disclaimer, the term of this patent is extended or adjusted under 35 U.S.C. 154(b) by 1204 days.

(21) Appl. No.: 16/883,858

(22) Filed: May 26, 2020

Related U.S. Application Data

(60) Provisional application No. 62/853,500, filed on May 28, 2019.

(51) Int. Cl.
| | |
|---|---|
| *G16H 50/70* | (2018.01) |
| *G06N 20/20* | (2019.01) |
| *G16H 40/20* | (2018.01) |

(52) U.S. Cl.
CPC ............. *G16H 50/70* (2018.01); *G06N 20/20* (2019.01); *G16H 40/20* (2018.01)

(58) Field of Classification Search
CPC ........ G16H 50/70; G16H 40/20; G16H 50/20; G16H 50/30; G06F 16/9577; G06F 3/0482; A61B 5/7267; G06Q 10/10; G01C 19/5776; G06N 20/00; G06N 20/10; G06N 20/20

See application file for complete search history.

(56) References Cited

U.S. PATENT DOCUMENTS

| | | | |
|---|---|---|---|
| 8,949,082 B2 * | 2/2015 | Farooq ................... | G16H 50/70 703/2 |
| 10,811,139 B1 * | 10/2020 | Wang ..................... | G06N 20/20 |
| 11,317,292 B1 | 4/2022 | Feldmann et al. | |
| 11,381,506 B1 | 7/2022 | Jindal et al. | |
| 11,621,085 B1 * | 4/2023 | Gottula .................. | G16H 50/50 706/11 |
| 2008/0155386 A1 | 6/2008 | Jensen | |

(Continued)

FOREIGN PATENT DOCUMENTS

| | | | | |
|---|---|---|---|---|
| AU | 2014239852 A1 | * | 11/2015 | ......... G06F 19/3437 |
| CA | 3109754 A1 | * | 3/2020 | .......... A61M 5/1723 |

(Continued)

*Primary Examiner* — Steven P Sax
(74) *Attorney, Agent, or Firm* — Kory D. Christensen

(57) ABSTRACT

In some examples, a prediction is generated by a prediction system. A machine learning model of the prediction system receives as input one or more data elements of a user service record, and outputs a prediction, the prediction corresponding to one or more probability scores. The one or more probability scores correspond to a prediction that a user will exhibit a certain behavioral pattern (e.g., probability of readmission to a service unit within a predefined post-release time period) and/or be classified into a certain service category (e.g. probability of association with a particular service group, the service group being included within a set of qualifying service groups). The prediction system may then provide the prediction to a user device of a user coordinator for subsequent presentation on the user device to assist the user coordinator in coordinating user service.

7 Claims, 20 Drawing Sheets

(56) References Cited

U.S. PATENT DOCUMENTS

| | | | |
|---|---|---|---|
| 2011/0313788 A1* | 12/2011 | Amland | G16H 50/20 |
| | | | 705/3 |
| 2012/0303827 A1 | 11/2012 | Neystadt et al. | |
| 2013/0144641 A1* | 6/2013 | Bessette | G06Q 10/10 |
| | | | 705/2 |
| 2013/0191158 A1* | 7/2013 | Fillmore | G16H 50/30 |
| | | | 705/3 |
| 2014/0350967 A1* | 11/2014 | Geleijnse | G16H 50/30 |
| | | | 705/3 |
| 2016/0094410 A1 | 3/2016 | Anwar et al. | |
| 2017/0083626 A1* | 3/2017 | Kensel | G06F 16/9577 |
| 2017/0323472 A1* | 11/2017 | Barnes | G01C 19/5776 |
| 2019/0209022 A1* | 7/2019 | Sobol | A61B 5/1112 |
| 2019/0231280 A1* | 8/2019 | Tudor | A61B 5/7267 |
| 2022/0385581 A1 | 12/2022 | Delos Reyes et al. | |

FOREIGN PATENT DOCUMENTS

| | | | | |
|---|---|---|---|---|
| CA | 2905637 C | * | 4/2022 | A61B 5/0013 |
| CA | 2945143 C | * | 8/2023 | G06Q 10/06 |
| EP | 3547327 A1 | * | 10/2019 | G06N 20/00 |
| EP | 3573068 A1 | * | 11/2019 | G16H 10/60 |
| WO | WO-2018146870 A1 | * | 8/2018 | G06Q 30/02 |

\* cited by examiner

1200

1204  1206  1202  1208

| West Florida Division / Oak Hill / Interventions | | | | | | | | |
|---|---|---|---|---|---|---|---|---|
| CJR▼ | Any Folder | Index 0 | Active 0 | Schedule 19 | Holding 45 | Follow-up 0 | Assured 136 | Archived 17 | Excluded 4 |

1210

Patient ▼ | Search by Patient | Status | -- Any -- ▼ | Search
Select Filter ▼ | App Status ▼ | Min Date | ✕ ▦ | Max Date | ✕ ▦

Intervention Date DESC ▼    ◀ Page 1 ▼ of 23 ▶    Export to CSV 1212  1216  1220  1222

| ☐ Intervention ▼ | Location | Patient | Status | Risk | Programs | 🔔 |
|---|---|---|---|---|---|---|
| ☐ CJR<br>schedule<br>#3270781<br>(current) by<br>CIERPKA LISA<br>on 07/05/2018 17:17 | K.6F<br>K.605-A | Joe D. | DIS IN<br>A:06/30/2018 13:40<br>D:07/04/2018 13:14<br>DisCode:RFU | >30%<br>Score:<br>0.26 | CJR<br>#3270781 (latest) schedule by CIERPKA<br>LISA on 07/05/2018 17:17 | ＋<br>F |
| ☐ CJR<br>schedule<br>#3268984<br>(current) by<br>CIERPKA LISA<br>on 07/05/2018 17:43 | K.6F<br>K.625-A | Rhett. B | DIS IN<br>A:07/03/2018 11:29<br>D:07/04/2018 15:36<br>DisCode:HHS | 21%<br>Score:<br>0.32 | CJR<br>#3268984 (latest) schedule by CIERPKA<br>LISA on 07/05/2018 17:43 | ＋<br>F |
| ☐ CJR<br>schedule<br>#3258708<br>(current) by<br>CIERPKA LISA<br>on 07/02/2018 16:45 | K.6F<br>K.605-A | Lisa M. | DIS IN<br>A:06/29/2018 08:05<br>D:06/30/2018 16:51<br>DisCode:HHS | 26%<br>Score:<br>0.09 | CJR<br>#3258708 (latest) schedule by CIERPKA<br>LISA on 07/02/2018 16:45 | ＋<br>F |
| ☐ CJR<br>schedule<br>#3250538<br>(current) by<br>CIERPKA LISA<br>on 07/02/2018 16:28 | K.6F<br>K.622-A | Mary T. | DIS IN<br>A:06/26/2018 09:27<br>D:06/29/2018 16:55<br>DisCode:HHS | 25%<br>Score:<br>0.11 | CJR<br>#3250538 (latest) schedule by CIERPKA<br>LISA on 07/02/2018 16:28 | ＋<br>F |

| Admission Date Time | Time Patient Flagged | COID | Coid Name | Pat Acct Num | Score | DRG Family Top Prediction |
|---|---|---|---|---|---|---|
| 2018-10-21 14:04:03 | 2018-10-21 14:04:03 | 30927 | OCALA REGIONAL MEDICAL CENTER | 22321 | 0.967 | HipFemurExceptM |
| | | 30997 | OAK HILL HOSPITAL | 52321 | 0.292 | HeartFailShock |
| | | 36957 | MEMORIAL HOSPITAL JACKSONVILLE | 68890 | 0.845 | ChronicObstrucP |
| | | 38329 | MEDICAL CITY DENTON | 01876 | 0.789 | HeartFailShock |
| | | 38340 | BAYSHORE MEDICAL CENTER | 21456 | 0.903 | SepticemiaSever |
| 2018-10-21 14:04:03 | 2018-10-21 11:05:47 | 08385 | REGIONAL MEDICAL CENTER | 61432 | 0.810 | KidneyUrinaryT1 |
| | | 25067 | ST. DAVID'S GEORGETOWN | 34517 | 0.229 | SepticemiaSever |
| | | 25960 | HEART HOSPITAL OF AUSTIN | 76143 | 0.213 | HeartFailShock |
| | | 26330 | WESTLEY WOODLAWN HOSPIT. | 45618 | 0.248 | HeartFailShock |
| | | 26910 | TOMBALL REGIONAL MEDICA. | 22334 | 0.218 | SepticemiaSever |
| | | 26935 | MEDICAL CITY WEATHERFORD | 62321 | 0.801 | CardiacArrhythC |
| | | 30504 | WEST HILLS HOSPITAL & MED. | 77890 | 0.957 | SepticemiaSever |
| | | 30908 | WESTSIDE REGIONAL MEDIC. | 21876 | 0.632 | SepticemiaSever |
| | | 30913 | ORANGE PARK MEDICAL CEN. | 20456 | 0.668 | SepticemiaSever |
| | | 30927 | OCALA REGIONAL MEDICAL CENTER | 65432 | 0.526 | HeartFailShock |
| | | | | 39517 | 0.987 | HipFemurExceptM |
| | | | | | 0.957 | SepticemiaSever |

FIG. 16

PREDICTIVE MODELING FOR ENHANCED DECISION MAKING

CROSS-REFERENCE TO RELATED APPLICATION

This application claims the benefit of and priority to U.S. Provisional Application No. 62/853,500, filed May 28, 2019, which is hereby incorporated by reference in its entirety for all purposes.

BACKGROUND

The amount of data generated each day continues to grow. In some environments, some of this data may be stored, while a majority of it may be evaluated and abandoned or ignored. Users and computing devices are beginning to rely more and on this data to make decisions. This may be especially true when the data is introduced as part of an operational flow. However, the time required to sort through stored data can create inefficiencies and the fact that other data may typically be ignored or abandoned may create undesirable service results.

This application incorporates the entire disclosure U.S. Provisional Application 62/853,500, filed on May 23, 2019, by reference in its entirety for all purposes.

SUMMARY

Exemplary embodiments described herein provide techniques for providing a probability score that a user will be readmitted to one of a plurality of units within a particular time period that follows a service provided for a present admission. A prediction system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a computer-implemented method. The computer-implemented method also includes receiving, by a prediction system, admission data may include a user identifier and a user admission time, the user admission time corresponding to a time a user was admitted to a unit of a plurality of associated units to receive service for a present admission. The method also includes retrieving, by the prediction system, based on the user identifier, a user profile of the user, the user profile may include a plurality of data elements. The method also includes inputting, by the prediction system into a machine learning model of the prediction system, a data element of the user profile. The method also includes determining, by the machine learning model of the prediction system, based on the data element, a probability score that the user will be readmitted to one of the plurality of associated units within a particular time period that follows the service for the present admission. The method also includes providing, by the prediction system, the probability score to a user device of a user coordinator of the plurality of associated units for subsequent presentation on the user device. Other embodiments of this aspect include corresponding computer systems, apparatus, and computer programs recorded on one or more computer storage devices, each configured to perform the actions of the methods.

Other objects, advantages, and novel features of the present invention will become apparent from the following detailed description of the invention when considered in conjunction with the accompanying drawings.

BRIEF DESCRIPTION OF THE DRAWINGS

Various examples in accordance with the present disclosure will be described with reference to the drawings, in which:

FIG. 12 is an example diagram illustrating a graphic user interface (GUI) for providing a probability score that a user will be readmitted to a unit, according to at least one example;

FIG. 16 is an example diagram illustrating a GUI for providing a probability score that a user will be readmitted to a unit, according to at least one example;

DETAILED DESCRIPTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes may be made in the function and arrangement of elements without departing from the spirit and scope as set forth in the appended claims.

Figure 1:
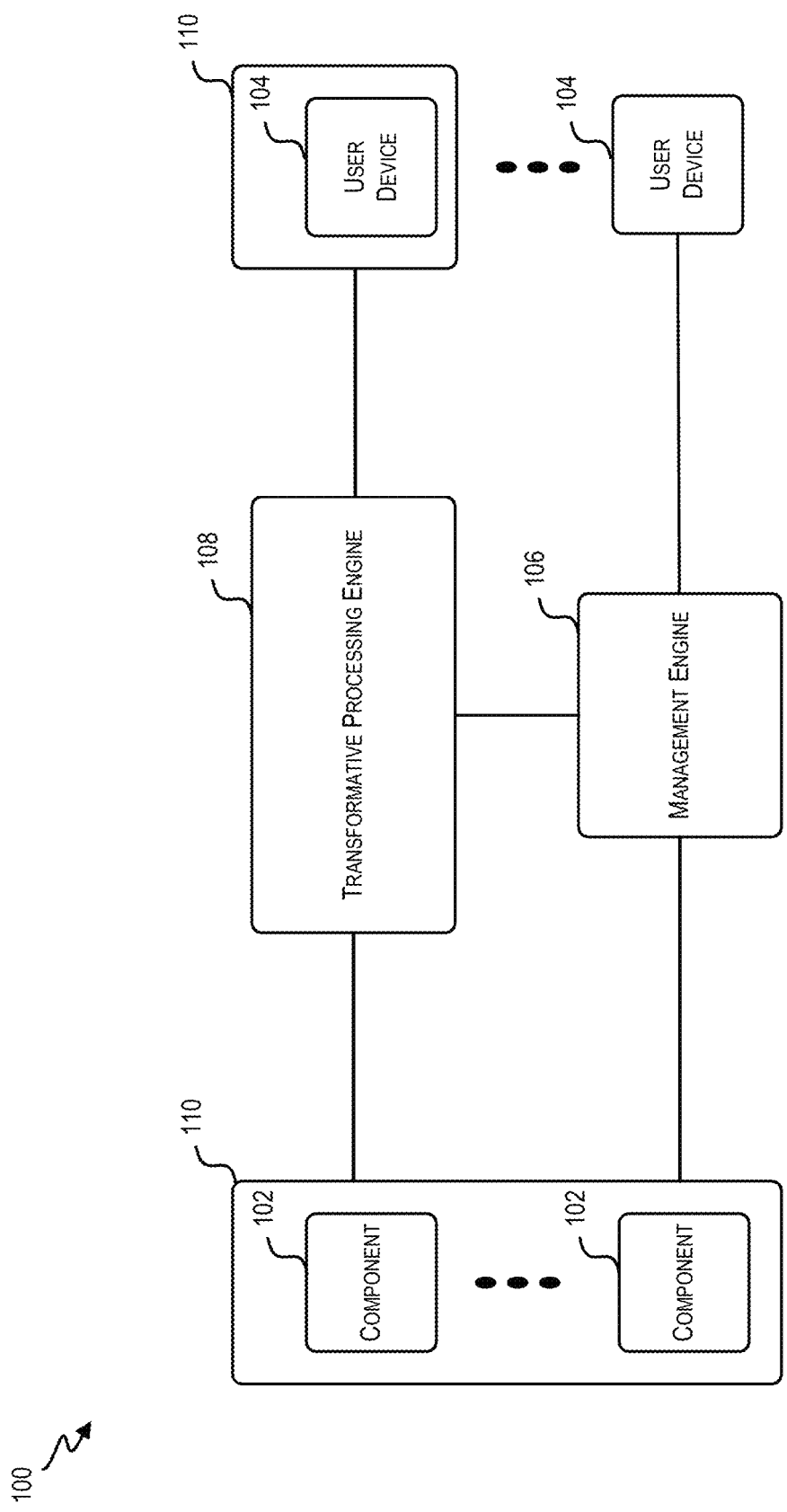
FIG. 1 is an example block diagram illustrating an interaction system in which techniques relating to providing a probability score that a user will be readmitted to a unit may be implemented, according to at least one example.

Referring first to FIG. 1, a block diagram of an example of an interaction system 100 is illustrated. Generally, in interaction system 100, data can be generated at one or more system components 102 and/or user devices 104. Management engine 106 can manage the flow of communications within interaction system. Transformative processing engine 108 can receive, intercept, track, integrate, process, and/or store such data.

Data flowing in interaction system 100 can include a set of communications. Each of one, some of all communications can include (for example) an encoding type, authentication credential, indication of a content size, identifier of a source device, identifier of a destination device, identifier pertaining to content in the communication (e.g., an identifier of an entity), a processing or reporting instruction, a procedure specification, transmission time stamp, and/or sensor measurement. Data may, or may not, selectively pertain to a particular entity and/or client. Data can, depending on the implementation, include individually identifiable information and/or de-identified information as it pertains to an entity and/or client. Data may, but need not, include protected information.

For example, a system component 102 can include, for example, a sensor to detect a sensor measurement and can thereafter generate and transmit a communication that reflects the sensor measurement. The communication may be transmitted at routine times and/or upon detecting a threshold (e.g., one or more) number of measurements or a measurement satisfying a transmission condition (e.g., exceeding a threshold value). In some instances, the sensor measurement corresponds to one reflecting a property of an object or entity (e.g., person) near the sensor. The communication may then include an identifier of the object or entity. The identifier can be determined, for example, based on detection of a nearby electronic tag (e.g., RFID tag), a detected user input received at a user interface of component 102, and/or data in a corresponding communication received from a user device.

As another example, a user device 104 can be configured to detect input received at an interface of the device. The input can include, for example, an identifier of an object or entity, an instruction, a characterization of an object or entity, an identification of an assessment to be performed, a specification of an aggregation or data processing to be performed, and/or an identification of a destination for a data-analysis report. User device 104 can further be configured to detect input requesting particular data, to generate a request communication (e.g., to be sent to transformative processing engine), to receive the requested data and/or to present the received data.

The depicted engines, devices and/or components can communicate over one or more networks. A network of one or more networks can include a wired network (e.g., fiber, Ethernet, powerline ethernet, ethernet over coaxial cable, digital signal line (DSL), or the like), wireless network (e.g., Zigbee™, Bluetooth™, WiFi™, IR, UWB, WiFi-Direct, BLE, cellular, Long-Term Evolution (LTE), WiMax™, or the like), local area network, the Internet and/or a combination thereof. It will be appreciated that, while one or more components 102 and one or more user devices 104 are illustrated as communicating via transformative processing engine 108 and/or management engine 106, this specification is not so limited. For example, each of one or more components 102 may communicate with each of one or more user devices 104 directly via other or the same communication networks.

A component 102 can be configured to detect, process and/or receive data, such as environmental data, geophysical data, biometric data, chemical data (e.g., chemical composition or concentration analysis data), and/or network data. The data can be based on data detected, for example, via a sensor, received signal or user input. A user device 104 can include a device configured to receive data from a user and/or present data to a user. It will be appreciated that, in some instances, a component 102 is also a user device 104 and vice-versa. For example, a single device can be configured to detect sensor measurements, receive user input and present output.

A component 102 can be configured to generate a communication that is in one or more formats, some of which can be proprietary. For example, an imaging machine (e.g., one of one or more components 102) manufactured by company A, located within a first facility (e.g., facility 110), and belonging to a first client, may save and transfer data in a first format. An imaging machine (e.g., one of one or more components 102) manufactured by company B, located within the first facility (e.g., facility 110), and belonging to the first client, may save and transfer data in a second format. In some examples, data from certain components is transformed, translated, or otherwise adjusted to be recognizable by transformative processing engine 108. Thus, continuing with the example from above, when the imaging machines manufactured by companies A and B are located within the first facility belonging to the first client, they may nevertheless save and transfer data in different formats. In some examples, one or more components 102 communicate using a defined format.

In some examples, each of one or more components 102 are each associated with one or more clients within a same or different interaction systems. For example, certain ones of one or more components 102 may be associated with a first client, while other ones of one or more components 102 may be associated with a second client. Additionally, each of one or more components 102 may be associated with a facility 110 (e.g., client facility). Each facility 110 may correspond to a single location and/or focus. Exemplary types of facilities include server farm facilities, web-server facilities, data-storage facilities, telecommunication facilities, service facilities, and/or operational facilities. For example, a first facility may include a structure at a first location at which one or more resources (e.g., computational resources, equipment resources, laboratory resources, and/or human resources) are provided. Each of the one or more resources may be of a first type in a first set of types. A resource type can be identified based on, for example, a characteristic of the resource (e.g., sensor inclusion) and/or a capability of providing each of one or more services. Thus, for example, resources at a first facility may be better configured for handling a particular type of service requests compared to those in another facility. As another example, different facilities may include resources of similar or same types but may vary in terms of, for example, accessibility, location, etc.

Transmission of data from one or more components 102 to transformative processing engine 108 may be triggered by a variety of different events. For example, the data may be transmitted periodically, upon detection of an event (e.g., completion of an analysis or end of a procedure), upon detection of an event defined by a rule (e.g., a user-defined rule), upon receiving user input triggering the transmission, or upon receiving a data request from transformative processing engine 108. Each transmission can include, e.g., a single record pertaining to a single entity, object, procedure, or analysis or multiple records pertaining to multiple entities, objects, procedures, or analyses.

In some examples, at least some of one or more user devices 104 are associated with facility 110. In some examples, at least some of one or more user devices 104 need not be associated with facility 110 or any other facility. Similar to one or more components 102, one or more user devices 104 may be capable of receiving, generating, processing, and/or transmitting data. Examples of one or more user devices 104 include, for example, a computer, a mobile device, a smart phone, a laptop, an electronic badge, a set-top box, a thin client device, a tablet, a pager, and other similar user devices). One or more user devices 104 may be configured to run one or more applications developed for interacting with data collected by transformative processing engine 108. For example, those user devices of one or more user devices 104 that are not associated with facility 110 may be configured to run one or more third-party applications that may rely in part on the data gathered by transformative processing engine 108.

Each of one or more components 102 and one or more user devices 104 may be utilized by one or more users (not shown). Each of the one or more users may be associated with one or more clients. For example, one of the one or more users can be associated with a client as a result of being employed by the client, physically located at a location of the client, being an agent of the client, or receiving a service from the client.

In some examples, one or more components 102 and one or more user devices 104 may communicate with transformative processing engine 108 and management engine 106 via different information formats, different proprietary protocols, different encryption techniques, different languages, different machine languages, and the like. As will be discussed with reference to FIG. 2, transformative processing engine 108 is configured to receive these many different communications from one or more components 102, and in some examples from one or more user devices 104, in their native formats and transform them into any of one or more formats. The received and/or transformed communications can be transmitted to one or more other devices (e.g., management engine 106, an entity device, and/or a user device) and/or locally or remotely stored. In some examples, transformative processing engine 108 receives data in a particular format (e.g., the HL7 format) or conforming to any other suitable format and/or is configured to transform received data to conform to the particular format.

One or more components 102 of facility 110 can include and/or has access to a local or remote memory for storing generated data. In some examples, the data is stored by one or more servers local to facility 110. The record service can be granted access to the data generated and/or transmitted by one or more components 102. In some examples, the record service includes a server or a plurality of servers arranged in a cluster or the like. These server(s) of the record service can process and/or store data generated by one or more components 102. For example, one or more records can be generated for each entity (e.g., each record corresponding to a different entity or being shared across entities). Upon receiving a communication with data from a component (or facility), the record service can identify a corresponding record and update the record to include the data (or processed version thereof). In some examples, the record service provides data to transformative processing engine 108.

Irrespective of the type of facility, facility 110 may update data, maintain data, and communicate data to transformative processing engine 108. At least some of the data may be stored local to facility 110.

A user interacting with a user device 104 can include, for example, a client customer, client agent and/or a third party. A user may interact with user device 104 and/or component 102 so as to, for example, facilitate or initiate data collection (e.g., by a component 102), provide data, initiate transmission of a data request, access data and/or initiate transmission of a data-processing or data-storage instruction. In some instances, one or more user devices 104 may operate according to a private and/or proprietary network or protocols. In other examples, one or more user devices 104 may operate on public networks. In any case, however, transformative processing engine 108 can have access to the one or more components and can communicate with them via a public, private, and/or proprietary network or protocols. The use of one or more private and/or proprietary protocols can promote secure transfer of data.

Figure 2:
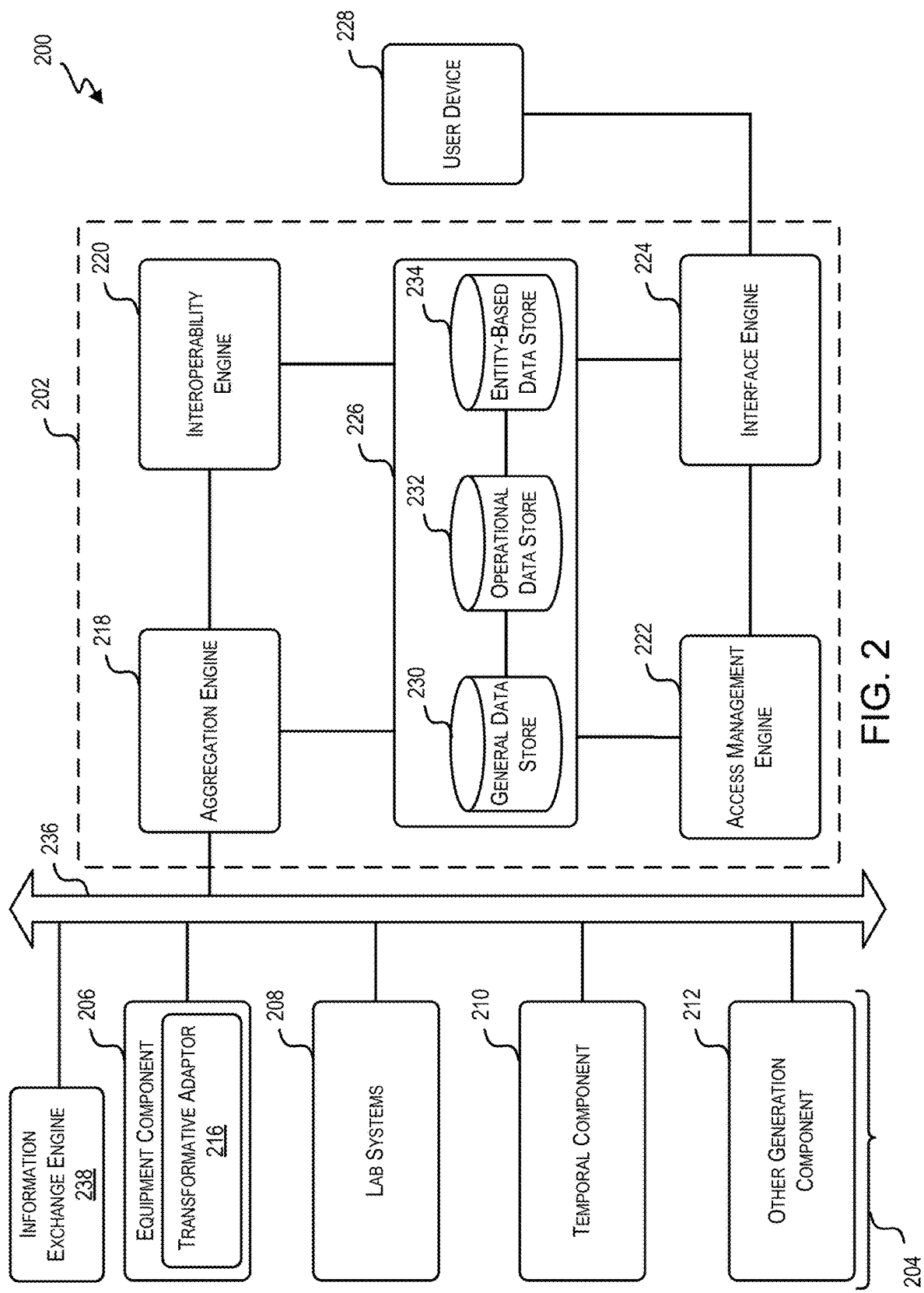
FIG. 2 is an example block diagram illustrating an interaction system in which techniques relating to providing a probability score that a user will be readmitted to a unit may be implemented, according to at least one example.

Referring next to FIG. 2, a block diagram of an example of an interaction system 200 is shown. Interaction system 200 includes a transformative processing engine 202. Transformative processing engine 202 is an example of transformative processing engine 108 discussed with reference to FIG. 1. Interaction system 200 also includes one or more generation components 204. In particular, one or more generation components 204 include an equipment component 206, a lab systems component 208, a temporal component 210, and other generation component 212. One or more generation components 204 are examples of one or more components 102 discussed with reference to FIG. 1. In some examples, the data may pass to the transformative processing engine 202 via an information exchange service bus 236 (e.g., an enterprise service bus). In some examples, only a portion of the is passed via the information exchange service bus 236, while other portions are passed directly to the transformative processing engine 202 without first passing over the information exchange service bus 236.

Generally, one or more generation components 204 includes any suitable device or system capable of generating data in the context of an interaction system. For example, the other generation component 212 may include a sensor on a door, and equipment component 206 may include a sophisticated computer-controlled laser device. In either case, each generation component generates some type of data. For example, the data provided by the sensor may be used to address security concerns or assessing heating, ventilating, and air conditioning (HVAC) costs for an institution. The data provided by the laser device may have been provided while engaged in a procedure and may then be used by other entities in the future to decide how to use the device.

As discussed in further detail herein, data generated by one or more generation components 204 can be of a variety of formats, some of which may be proprietary. For example, a single component can generate data in multiple formats, different components can generate data in different formats, and/or different component types can result in generation of data in different formats. In some instances, formatting of a data can depend on a service having been provided, a user initiating data generation, a destination to receive the data, a location at which a service was provided, etc. In some examples, a typical interaction system includes thousands of generation components producing data in hundreds of formats. In order to harness the power that comes from such a large amount of data to make informed decisions, it is desirable that all, or at least a large portion of the data, is shared. Use of transformative processing engine 202 in accordance with techniques described herein may achieve this design-making large amounts of data, in many different originating formats available to various types of users, via one or more interfaces. At least a portion of the data generated by the generation components 204 may be provided to the transformative processing engine 202. In some examples, each generation component 204 includes an agent that executes on the generation components 204 and determines which data to send to the transformative processing engine 202 and other engines described herein. In some examples, the generation components 204 provide data to the transformative processing engine 202 via a messaging bus (e.g., an information exchange service bus 236). The messaging bus, which may be included in the transformative processing engine 202 or separate, is able to see data that moves throughout the interaction system 200. The information exchange service bus 236 also includes a subscription registry that can be used to manage subscriptions to the information exchange service bus 236 for certain data (e.g., data having certain characteristics). The information exchange service bus 236 may send and/or direct data to certain other entities when appropriate as indicated by subscription records in the registry.

While one or more generation components 204 are illustrated adjacent to each other, it is understood that each may be located within one facility or that the components may be spread out among many facilities. In addition, in some examples, one or more generation components 204 belong to different clients.

Turning now to equipment component 206, this component includes any machine, contrivance, implant, or other similar related article, that is intended to aid in reaching a particular objective. In some instances, equipment component 206 includes one or more sensors to detect environmental or other stimuli. Equipment component 206 can include, for example, equipment to monitor a stimulus, detect stimulus changes, detect stimulus-indicative values, and so on. Exemplary equipment components 206 include an imaging device, a device that detects and characterizes electrical signals, a device that detects pressure, and/or a device that detects concentration of one or more particular elements, compounds and/or gases.

As illustrated, equipment component 206 includes transformative adaptor 216. In some examples, transformative adaptor 216 is a device that transforms, translates, converts, or otherwise adjusts output data from equipment component 206. For example, an equipment component 206 can be a scanner that outputs its results in format A, but the majority of other scanners in the interaction system output their results in format B. Transformative adaptor 216 may be implemented to convert or otherwise adjust the results in format A to conform closer to format B. For example, the conversion from format A to format B may be performed using a conversion rule, which may be user-define or learned. Transformative processing engine 202 may perform similar tasks as it relates to all data generated within interaction system 200. In this manner, transformative adaptor 216 can perform an initial step in the process of transformation, translation, conversion, or adjustment of the output of equipment component 206. In some examples, transformative adaptor 216 is implemented in hardware, software, or any suitable combination of both. In some examples, other transformative adaptors (not shown) may be implemented within others of one or more generation components 204. In some examples, equipment component 206 may not include transformative adaptor 216.

Lab systems component 208 includes any suitable laboratory equipment or system that is intended to analyze material, such as biological material. This includes, for example, laboratory equipment that analyzes biological samples; electric microscopes; ultracentrifuges; data collection devices, including Kymographs, sensors connected to a computer to collect data; monitoring devices; computers used to report results of lab tests, and other similar laboratory equipment. Each of the above-listed components generates data that is provided (directly or indirectly) to transformative processing engine 202.

Temporal component 210 may include any suitable computing devices used with respect to interaction system 200. For example, temporal component 210 can be configured to allocate a resource to a particular entity during a particular temporal window. Temporal component 210 can monitor a schedule for the resource and can identify one or more available temporal windows that may be secured by a particular entity. Upon receiving an indication, temporal component 210 may update a schedule of a resource to reflect that a particular temporal window is to be allocated for service of a particular entity.

Each of one or more generation components 204 and the user device 228 may include individual and/or shared storage systems, one or more processors, a user interface, a network connectivity device, and one or more ports. The storage system include memory that may be implemented, e.g., using magnetic storage media, flash memory, other semiconductor memory (e.g., DRAM, SRAM), or any other non-transitory storage medium, or a combination of media, and can include volatile and/or non-volatile media. The storage systems may also be configured to store computer-executable code or instructions for interacting with the user interface and/or for one or more applications programs, such as an application program for collecting data generated by the particular generation component.

The one or more processors may be configured to access the operating system and application programs stored within the storage systems, and may also be configured to execute such program code. The one or more processors can be implemented as one or more integrated circuits, e.g., one or more single-core or multi-core microprocessors or microcontrollers, examples of which are known in the art. In operation, the one or more processors can control the operation of the particular component. The one or more processors may access and execute the program code and at any given time.

The user interface can include any combination of input and output devices. In some instances, a user can operate input devices of the user interface to invoke the functionality of the particular component or user device. For example, the user interface may enable the user to view, hear, and/or otherwise experience output from component or user device via the output devices of the user interface. Examples of output devices include a display, speakers, and the like.

The network connectivity device may enable the component or user device to communicate with transformative processing engine 202 and other components or other user devices via one or more networks. The one or more networks may include any suitable combination of cable, cellular, radio, digital subscriber line, or any other suitable network, which may be wired and/or wireless. In some examples, the network connectivity device may enable the component or the user device to communicate wirelessly with various other components and/or transformative processing engine 202. For example, the components may include circuitry to enable data communication over a wireless medium, e.g., using near-field communication (NFC), Bluetooth Low Energy, Bluetooth® (a family of standards promulgated by Bluetooth SIG, Inc.), Zigbee, Wi-Fi (IEEE 802.11 family standards), or other protocols for wireless data communication.

The one or more ports may enable the component or the user device to receive data from one or more sensors. The sensors may be any suitable type of sensor to capture data. Such captured data may be shared with transformative processing engine 202 in accordance with techniques described herein. In some examples, the sensors may also be configured to detect the location and other details about the component or the user device. In some examples, the component and the user device may include global positioning chips that are configured to determine a geolocation.

Transformative processing engine 202 includes an aggregation engine 218, an interoperability engine 220, an access management engine 222, an interface engine 224, and a data store 226. Generally aggregation engine 218 is configured to collect data from multiple communications. The data may be from one or multiple generation components 204 and/or may be of same or different formats. Aggregation engine 218 may be configured to perform one or more operations on the collected data. For example, aggregation engine 218 may tag data, log data, perform protocol conversion, and may support one-to-many communications. The collection may be asynchronous. In some examples, the data has been saved locally in connection with one or more generation components 204 in many different formats having many different data structures.

Aggregation engine 218 can identify data to be aggregated based on, for example, intra-communication data, a current time, a source generation component, and/or one or more aggregation rules. For example, an aggregation rule may specify that data is to be aggregated across all communications that include content with a same entity identifier. An aggregation may be dynamic. For example, aggregated data may reflect that from within a most recent 12-hour period. Thus, an aggregation may be updated in time to exclude older data from the aggregation and to include newer data.

Aggregation engine 218 can be configured to provide data from one or more communications to interoperability engine 220. Interoperability engine 220 can be configured to perform one or more operations on the received data and store it in data store 226. For example, interoperability engine 220 may perform semantic tagging and indexing of data. This may include extracting field values from data, categorizing data (e.g., by type of data, characteristic of an entity, location of facility, characteristic of facility, and the like), anonymizing or partially-anonymizing data, and the like. Interoperability engine 220 may also include a high availability cache, an alerts engine, and a rules engine. In some examples, interoperability engine 220 operates synchronously.

From interoperability engine 220, data flows to data store 226. Data store 226 (and any other data store discussed herein) may include one or more data stores, which may be distributed throughout two or more different locations (e.g., present on different devices, which can include devices of different entities and/or a cloud server). In some examples, data store 226 includes a general data store 230, an operational data store 232, and an entity-based data store 234. Within each of the data stores 230, 232, and 234 is stored data. Depending on the structure of the particular data store, certain data stores may include rules for reading and writing. The data stores 230, 232, and 234 may include records, tables, arrays, and the like, which may be relational or non-relational. Depending on the data store, records for individual entities, business and analytics information, output data from one or more generation components 204, and the like may be retained. The data within the data stores 230, 232, and 234 include elements or tags such that a particular data (e.g., for a single entity, protocol, etc.) can be retrieved.

Access management engine 222 is configured to manage access to features of transformative processing engine 202, including access to the data retained in data store 226. For example, access management engine 222 may verify that a user device such as user device 228 is authorized to access data store 226. To verify the user device 228, access management engine 222 may require that a user of the user device 228 input a username and password, have a profile associated with the interaction system, and the like. Access management engine 222 may also verify that the user device 228 has an IP address or geographical location that corresponds to an authorized list, that the user device 228 includes a plug-in for properly accessing the data store 226, that the user device 228 is running certain applications required to access the data store 226, and the like.

Interface engine 224 is configured to retrieve the data from data store 226 and provide one or more interfaces for interacting with elements of transformative processing engine 202. For example, interface engine 224 includes an interface by which an application running on user device 228 can access portions of data within data store 226.

As described herein, an information exchange engine 238 shares a network connection with the information exchange service bus 236. The information exchange engine 238 is configured to monitor data (e.g., messages) that is passed over the information exchange service bus 236 and, from the monitored data, select certain portions to provide to one or more authorized user devices. The information exchange engine 238 is also configured to route inbound messages and route outbound messages, as described herein. The information exchange engine 238 is also configured to generate customized messages based on dependent user data.

Figure 3:
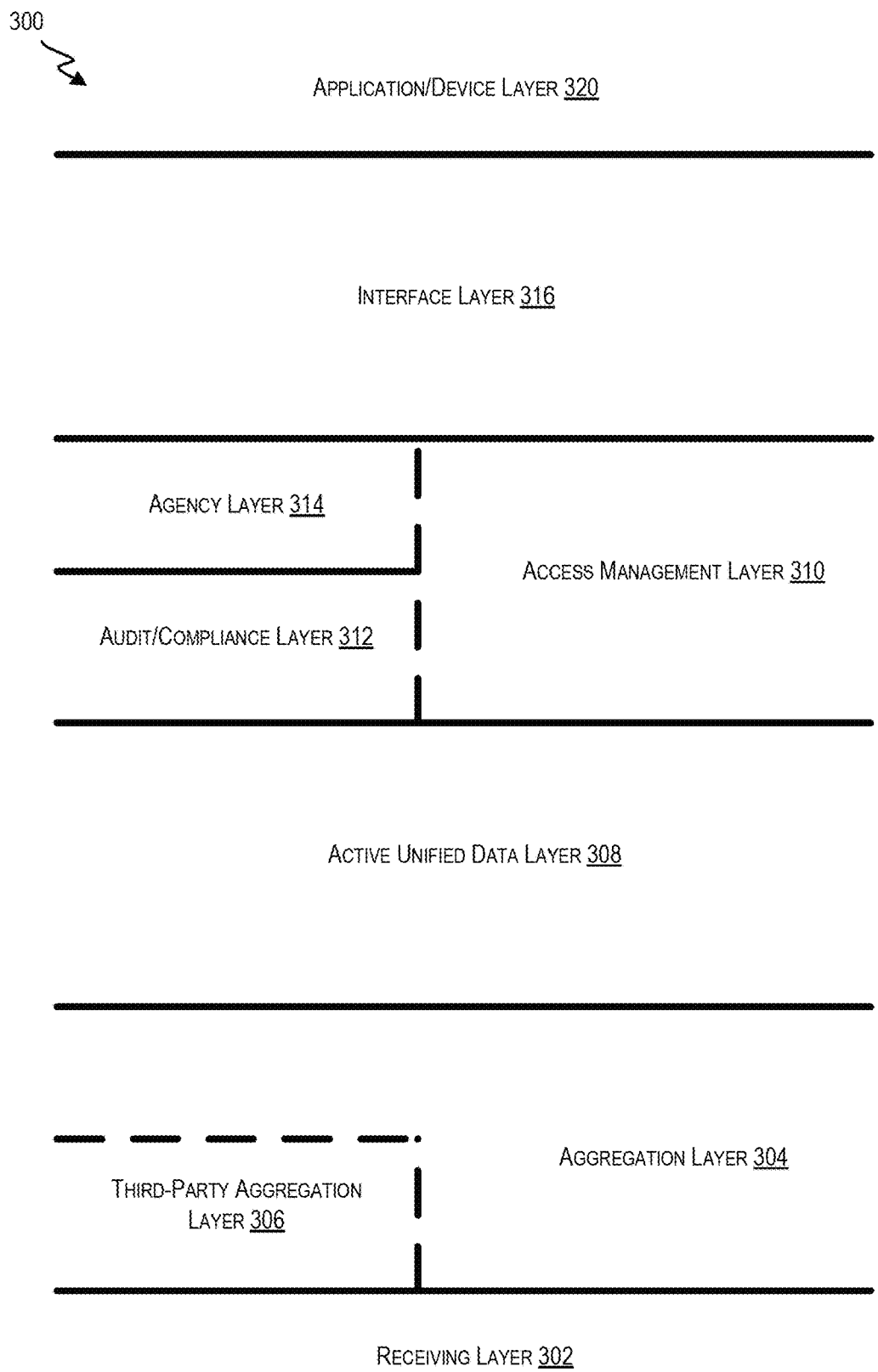
FIG. 3 is an example schematic model illustrating a network communication model in which techniques relating to providing a probability score that a user will be readmitted to a unit may be implemented, according to at least one example.

Turning next to FIG. 3, an architecture stack 300 is shown. In some examples, techniques relating management of data are implemented in accordance with architecture stack 300. And while architecture stack 300 is illustrated as having a particular structure, it is understood that other structures, including those with more or less layers than illustrated, is within the scope of this specification. In some examples, architecture stack 300 is implemented across an interaction system having a plurality of systems belonging to the same client or spread across different clients. Thus, architecture stack 300 can be used to integrate different systems of different organizations, entities, and the like and to provide a fluid sharing of information among elements within the interaction system and without the interaction system. In some instances, a multi-layer part of architecture stack 300 is implemented at a single system or device within an interaction system.

The different layers of architecture stack 300 will be described generally with reference to FIG. 3 and in detail with reference to subsequent figures. Architecture stack 300 includes a receiving layer 302 as the bottom-most layer. Receiving layer 302 includes receiving data from elements that share data with other elements within an aggregation layer 304. For example, as detailed herein, receiving layer 302 can include receiving data from generation components that generate data. As such, receiving layer 302 is where data that has been created is received. In some examples, the data within receiving layer 302 may be in its raw formats. The output may then be transmitted to aggregation layer 304. In some examples, components of receiving layer 302 may have complimentary layers to facilitate data transfer. For example, the components may include a data generation and/or a data transmission layer for providing data to receiving layer 302.

Elements of aggregation layer 304 aggregate the data generated by the elements of receiving layer 302. For example, the elements of aggregation layer 304 may include aggregation engines that collect data from generation components located within receiving layer 302. Such aggregation may be performed periodically, in response to a user request, according to a schedule, or in any other suitable manner. In some examples, data of aggregation layer 304 may be aggregated according to input and/or rules and may aggregate across records pertaining to, e.g., a facility, entity, time period, characteristic (e.g., demographic characteristic or condition), outcome, and any other suitable input and/or rules. The aggregation may include compiling the data, generating a distribution, generating a statistic pertaining to the data (e.g., average, median, extremum, or variance), converting the data, transforming the data to different formats, and the like.

Next, architecture stack 300 includes an active unified data layer 308. Elements of active unified data layer 308 receive data from the elements of the other layers and store such data in a unified manner. In some examples, this may include storing the data in a manner that allows for later searching and retrieval using a defined set of method calls, techniques, and or procedures. For example, the data may be stored such that a different application can access the data in a standard or unified manner. Thus, elements of active unified data layer 308 may receive information collected or generated within aggregation layer 304 and make certain adjustments to the data (e.g., translations, tagging, indexing, creation of rules for accessing the data, conversion of formatting of the data, generation of compressed versions, and the like) prior to retaining the data within one or more data stores accessible within active unified data layer 308.

Architecture stack 300 also includes an access management layer 310, which can include an audit/compliance layer 312 and/or an agency layer 314. Access management layer 310 includes elements to manage access to the data. For example, access management layer 310 may include elements to verify user login credentials, IP addresses associated with a user device, and the like prior to granting the user access to data stored within active unified data layer 308.

Audit/compliance layer 312 includes elements to audit other elements of architecture stack 300 and ensure compliance with operating procedures. For example, this may include tracking and monitoring the other elements of access management layer 310.

Agency layer 314 includes an access location (e.g., a virtual private network, a data feed, or the like) for elements of agencies that are interested in the operations of the interaction system in which architecture stack 300 is implemented. For example, agency layer 314 may allow a governmental entity access to some elements within architecture stack 300. This may be achieved by providing the governmental entity a direct conduit (perhaps by a virtual private network) to the elements of access management layer 310 and the data within active unified data layer 308. Audit/compliance layer 312 and agency layer 314 are sub-layers of access management layer 310.

Architecture stack 300 also includes interface layer 316. Interface layer 316 provides interfaces for users to interact with the other elements of architecture stack 300. For example, clients, entities, administrators, and others belonging to the interaction system may utilize one or more user devices (interacting within application/device layer 320) to access the data stored within active unified data layer 308. In some examples, the users may be unrelated to the interaction system (e.g., ordinary users, research universities, for profit and non-profit research organizations, organizations, and the like) and may use applications (not shown) to access the elements within architecture stack 300 via one or more interfaces (e.g., to access data stored within active unified data layer 308). Such applications may have been developed by the interaction system or by third-parties.

Finally, architecture stack 300 includes application/device layer 320. Application/device layer 320 includes user devices and applications for interacting with the other elements of architecture stack 300 via the elements of interface layer 316. For example, the applications may be web-based applications, entity portals, mobile applications, widgets, and the like for accessing the data. These applications may run on one or more user devices. The user devices may be any suitable user device as detailed herein.

Figure 4:
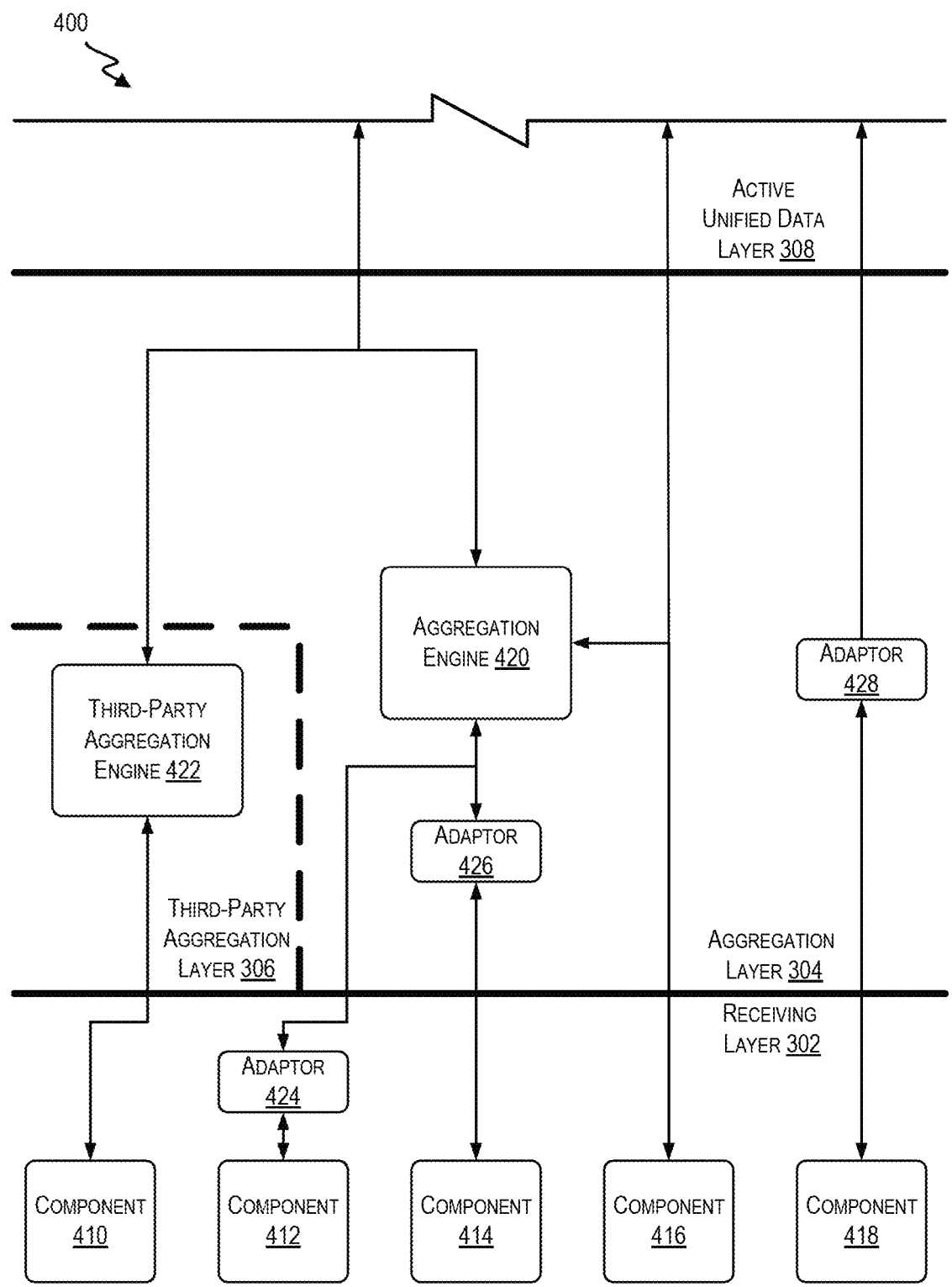
FIG. 4 is an example schematic model illustrating an aspect of the network communication model of FIG. 3 in more detail.

Turning next to FIG. 4, a diagram 400 is shown that depicts a portion of architecture stack 300 according to at least one example. In particular, the diagram 400 includes receiving layer 302, aggregation layer 304, aggregation layer 306, and a portion of active unified data layer 308. Receiving layer 302 receives data from one or more components 410-418. Components 410-418 are examples of one or more generation components 204. Components 410-418 may be spread across multiple facilities within a single or multiple clients. In some examples, components 410-418 may include complimentary layers to facilitate data transmission. For example, components 410-418 may include a transmission layer, generation layer, and/or a receiving layer to communicate data at receiving layer 302 and, in some examples, receive data from receiving layer 302.

In some instances, two or more of components 410-418 generate data according to different formats. The data can then be transformed, translated, or otherwise adjusted before an aggregation engine 420 (e.g., aggregation engine 218) or a third-party aggregation engine 422 (e.g., aggregation engine 218) collects the data. In some examples, the adjustment takes place within receiving layer 302. Thus, an adaptor 424 is associated with component 412 located in receiving layer 302. Adaptor 424 is an example of transformative adaptor 216. Adaptor 424 is implemented, as appropriate, in hardware, software, or any suitable combination of both. For example, transformative adaptor 216 may be a bolt-on adaptor that adjusts data as such data leaves component 412.

Other adaptors, such as adaptor 426 and adaptor 428, are implemented within aggregation layer 304. These adaptors can function in a similar manner as adaptor 424. In some examples, the data provided by component 414 is transmitted through adaptor 426 prior to being directed to aggregation engine 420. The data provided by component 416 is transmitted through aggregation layer 304 and/or enters aggregation engine 420 without having first traveled through an adaptor. The data provided by component 418 is transmitted through aggregation layer 304 and through adaptor 428. In some examples, component 418 provides for streaming of data. The data provided by component 410 is transmitted directly to third-party aggregation engine 422.

Aggregation engine 420 and third-party aggregation engine 422 function in a similar manner. In some examples, third-party aggregation engine 422 is operated by a different entity than the entity that operates aggregation engine 420 and may belong to different clients or a different interaction system. This may be because the data collected by third-party aggregation engine 422 differs in some way from the data collected by aggregation engine 420. In any event, aggregation engine 420 is configured to perform integration of data, including generic integration. For example, aggregation engine 420 performs one or more operations on data including tagging, logging, and protocol conversion. Aggregation engine 420 also supports one-to-many communications of data. In some examples, data flows between aggregation engine 420, the third-party aggregation engine 422, and some of components 410-418 and elements of active unified data layer 308.

The diagram 400 also includes the information exchange service bus 236 and the information exchange engine 238. As introduced herein, messages passing through the aggregation layer 304 can pass over the information exchange service bus 236. In this manner, the information exchange engine 238 can access the messages, route the messages, and/or customize the messages.

Figure 5:
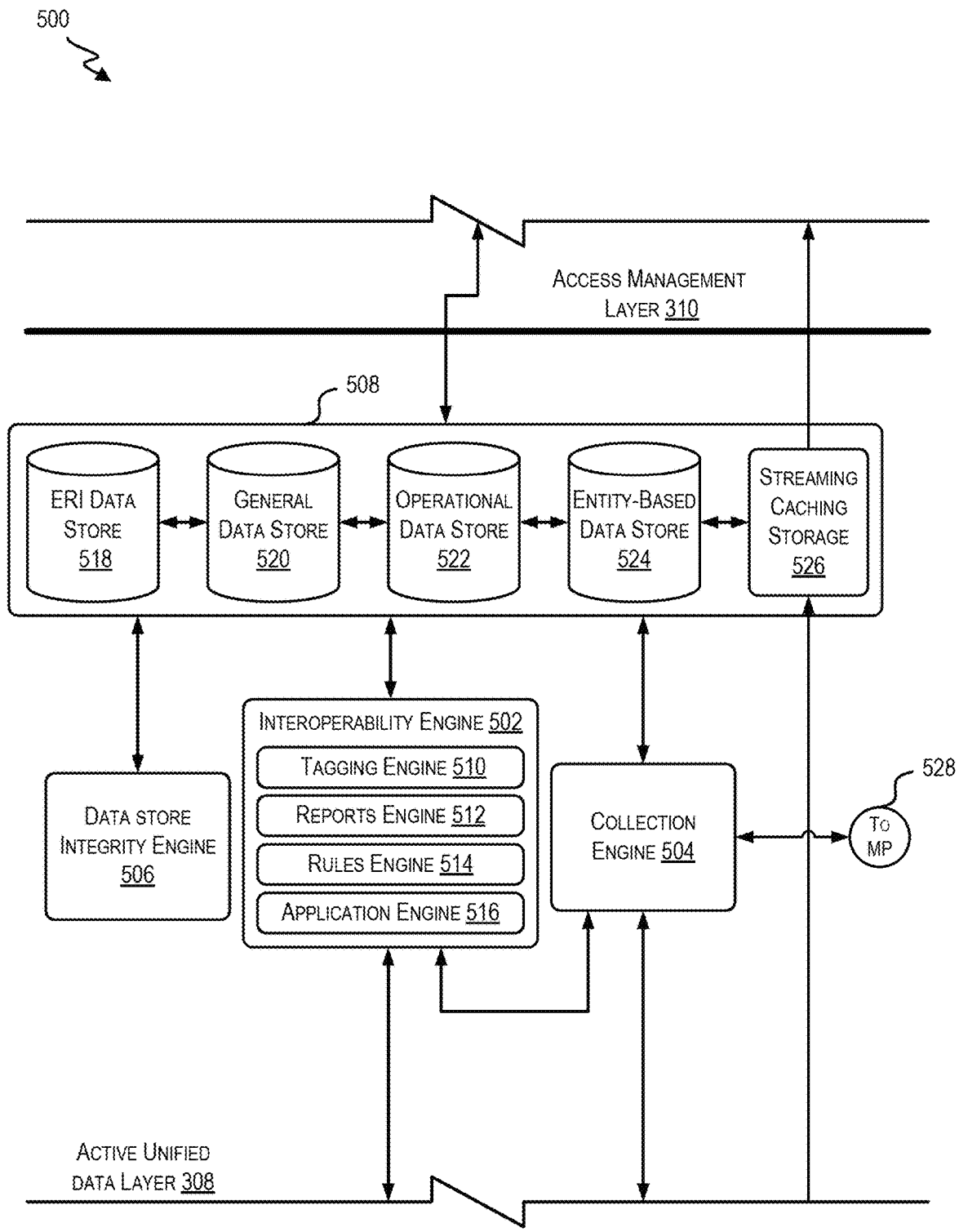
FIG. 5 is an example schematic model illustrating an aspect of the network communication model of FIG. 3 in more detail.

Referring next to FIG. 5, a diagram 500 is shown that depicts a portion of architecture stack 300 according to at least one example. In particular, diagram 500 includes active unified data layer 308 and a portion of access management layer 310. Active unified data layer 308, as illustrated in diagram 500, includes an interoperability engine 502 (e.g., interoperability engine 220), a collection engine 504, a data store integrity engine 506, and a data store 508 (e.g., data store 226). Generally, interoperability engine 502 receives data from elements within aggregation layer 304 (e.g., from aggregation engine 420) and performs one or more operations with respect to the data. Interoperability engine 502 also facilitates storage of at least a portion of the processed information in data store 508.

Collection engine 504 is configured to generate message indicators identifying flows of data by and between elements of an interaction system implemented using the techniques described herein. The flows of information include messages which include data, and the message indicators include unique message identifiers that can be used to identify the messages. The unique message identifiers include information that can be used to uniquely identify the messages. For example, a unique message identifier for a particular message can include a concatenation of the following information stored in a table: a source application, a facility, a message type, and a message control identification (ID). The unique message identifier can also be the message control ID. The unique message identifier may be created as messages including data are transmitted from aggregation layer 304.

In some examples, the table also includes information for tracking the progress of the message from an origination node to a destination node. For example, typically when a message (e.g., any communication of data) is first received by transformative processing engine 108 (e.g., interoperability engine 502), management engine 106 (e.g., collection engine 504 of management engine 106) may generate a unique identifier for the message in order to track that message as it moves throughout the interaction system. The unique identifier may be included in the header of the message such that when the next node (e.g., component, device, server, etc.) after transformative processing engine 108 receives the message, that node can report back to management engine 106 that it saw the message. In this manner, management engine 106 may track messages from end-to-end for the life of the message.

In one example, the messages are requests. The requests may be generated based om user input at one of the components. The requests may be received by transformative processing engine 108 and integrated into the system. In some examples, management engine 106 may be notified that the requests have been received and may therefore be configured to generate message IDs for each request. These message IDs may then be associated with each of the requests. As the requests continue to move throughout the interaction system (e.g., away from transformative processing engine 108), management engine 106 may track their movement using the message IDs. If one of the requests does not arrive at its destination, management engine 106 may determine why the request was stopped. In some examples, this cause may be hardware related (e.g., an unplugged Ethernet cable, a broken router, etc.), software related (e.g., a router routing to the wrong location), or any other reason for orders not arriving at their correct destination.

In some examples, management engine 106 (e.g., collection engine 504 of management engine 106) may receive the message and/or message identifier directly from one of components 410-418. For example, one of components 410-416 may be configured to generate the unique message identifier and/or communicate directly with management engine 106. The message also may travel via one or more intermediate nodes on its way to the destination node. In some examples, a node is a component such as components 410-418, which may be running an application. In some examples, the unique identifier and the routing of the message to its destination may be stored in a table that also includes: a geolocation of each node, a network from which the message originated, a type of node, the unique node identifier, and a time associated with the message leaving the origination node. In some examples, collection engine 504 provides unique message identifiers to other elements of the interaction system to monitor the messages as they move throughout the interaction system. Collection engine 504 also provides a portion of the unique message identifiers to a management platform (indicated by a circle 528) for further analysis of the message identifiers. Such analyses may include reconciliation of lost messages, latency reporting, audit management and compliance, and other such analyses.

As mentioned previously, interoperability engine 502 is configured to store data in data store 508. A plurality of sub-engines 510-516 of interoperability engine 502 are configured to perform operations relating to storing data in data store 508.

Interoperability engine 502 includes a tagging engine 510 configured to perform semantic tagging and indexing of data. Tagging engine 510 therefore is configured to receive data, read metadata associated with the data, semantically scan the content of the data, and associate one or more tags with the data. Tagging engine 510 may therefore have access to hundreds, thousands, or even more possible tags. These tags may have been input by users, learned, pre-defined, generated by outside third-party mapping sources, and/or gathered from other components and/or data stores of the interaction system. For example, if the data is a chart for an entity, the tagging engine may be configured to read any metadata associated with the chart to determine which tags may be appropriate to associate with the chart. From the metadata, tagging engine 510 may determine that the chart is for a type of entity by reading metadata indicating that an author field is populated with the name of another particular type of entity. Tagging engine 510 may have access to other data to compare the analyzed metadata against (e.g., to identify that the author's name corresponds to Dr. Brown who is an oncologist). Other examples, of metadata that may be included in one or more fields include author, document type, creation time and date, last update time and date, upload time and data, geographic location, unique ID associated with the client or facility where the data originated, and other similar fields. The tags may be stored in association with the data (e.g., the chart) and/or may be stored independent from the data but include an identifier such that when searching tags the data may be capable of population.

Continuing with the example from above, if the data is a chart for a first type of entity, tagging engine 510 may be configured to read the content of the chart to determine which tags may be appropriate to associate with the chart. For example, this may comprise analyzing the content of the chart (i.e., individual pages) semantically to look for artifacts (e.g., keywords, phrases, and the like) in the content. These artifacts may be identified by tagging engine 510 and used to decide which tags to associate with the document. In some examples, semantic scanning may involve filtering out words (e.g., articles, such as "a" and "the"), phrases, and the like. Similar to the reading of metadata, the tags may be pre-defined, user-defined, learned, and the like. In some examples, reading metadata associated with messages may provide meaning and/or give context to the particular record of data. This meaning and/or context may assist tagging engine 510 to determine one or more tags to associate with the data. The tags may be chosen, for example, based on values of particular fields in the data, detecting a frequency of one or more words in a document or metadata and/or of a set of related words (e.g., tagging a record with "cancer" upon detecting words such as tumor, metastasize, chemotherapy, radiation, oncology, malignant, stage 3, etc.). In this manner, tagging engine 510 may also index portions of the data within one or more data stores of data store 508. In some examples, such indexing may be based in part on the selected tags.

Interoperability engine 502 also includes a reports engine 512 configured to generate one or more reports or alerts based on data. For example, reports engine 512 may generate reports when certain types of data are received or when data with certain characteristics is received. Reports engine 512 may also generate alerts. The reports and/or alerts generated by reports engine 512 may be outputted in the form of one or more communications to an administrator, an authorized user, or other similar user via a user device. Such communications can include, for example, signals, sirens, electronic notifications, popups, emails, and the like. Content of such communications may include information characterizing a performance metric, efficiency and/or outcomes; identifying concerning patterns; identifying losses of data; and the like. In some examples, the content is presented in the form of one or more documents, tables, figures, charts, graphs, and the like.

Interoperability engine 502 also includes a rules engine 514 configured to create and manage condition-response rules, alert/reports rules, data-formatting rules, data-sharing rules, transmission rules, aggregation rules, user authorization rules, and other similar rules. Such rules may be user-defined, fixed, learned by elements of the interaction system, and any combination of the foregoing. Finally, interoperability engine 502 includes an application engine 516 configured to provide service-oriented architecture web services.

Data store 508 includes an electronic record information data store 518 ("ERI data store 518"), a general data store 520, an operational data store 522, an entity-based data store 524, and a streaming caching storage 526. While data store 508 is illustrated as including a fixed number of data stores and storage elements, it is understood that data store 508 can include any suitable number of data stores and storage elements, including more than illustrated or less than illustrated.

In some examples, a data query script is provided to query a first data store and/or to obtain data for populating a data store. Such script could query a data store described herein (e.g., data store 508) and/or could be used to obtain data to populate a data store described herein (e.g., data store 508). In one instance, the script is configured to be repeatedly executed, so as to repeatedly draw data from a source data store. The retrieved data can then be formatted, filtered, sorted and/or processed and then stored, presented and/or otherwise used. In this manner, the script can be used to produce streaming analytics.

In some instances, the data query script, when executed, identifies each of the data stores of interest. Identifying the data stores of interest involves identifying at least a portion of data from the data stores simultaneously and/or sequentially. For example, the script can identify corresponding data stores (e.g., or components of a single data store or multiple data stores) that pertain to one or more similar variables but that differ in one or more other variables. Once the portion of the data from the data stores is identified, a representation of the identified data can be output to one or more files (e.g., Extensible Markup Language (XML) files) and/or in one or more formats. Such outputs can then be used to access the data within one or more relational database accessible using Structured Query Language (SQL). Queries made using SQL can be made sequentially or in parallel. Results from an SQL query may be stored in a separate database or in an XML file that may be updated either in part or as a whole. The data query script may be executed periodically, in accordance with a user-defined rule, in accordance with a machine-defined or machine-learned rule, and in other suitable manner.

Within ERI record data store 518 is retained data. In some examples, the information within ERI record data store 518 is organized according to entity identifying information. Thus, ERI record data store 518, in some examples, includes individually identifiable information. But it may also include de-identified information.

Within general data store 520 is retained data. The data may be stored in a relational database format or in any other suitable format. Thus, the data within general data store 520 may be retained in a data structure that includes one or more tables capable of accessing each other. In some examples, general data store 520 includes a subset of the information that is included in operational data store 522.

Within operational data store 522 is retained data in a relational database format. Thus, the data within operational data store 522 may be retained in a data structure that includes one or more data structures (e.g., tables) capable of accessing each other. Operational data store 522 is an example of an operational data warehouse. In operational data store 522 is joined many different types of data. In some examples, the operational data store 522 includes data pertaining to decision making as discussed herein and other data typically used.

Within entity-based data store 524 is retained data in a non-relational database format. Thus, the data within entity-based data store 524 may be retained in a structure other than tables. Such structure may be appropriate for large and complex data sets. In some examples, entity-based data store 524 (or any other data store) may be a unified system, which may include: a document-centric, schema-agnostic, structure-aware, clustered, transactional, secure, database server with built-in search and a full suite of application services. An example of such a unified system may be Marklogic. Entity-based data store 524 can support data aggregation, data organization, data indexing, data tagging and mapping to semantic standards, concept matching, concept extraction, machine learning algorithms, concept discovery, concept mining, and transformation of record information. In some examples, entity-based data store 524 includes data pertaining to decision making (similar to general data store 520) as discussed that is organized and accessed in a different manner. For example, the data within entity-based data store 524 may be optimized for providing and receiving information over one or more information exchanges. In some examples, entity-based data store 524 includes a subset of the information that is included in operational data store 522.

Finally, in some examples, streaming caching storage 526 is a streaming data cache data store. As discussed previously, certain components of components 410-418 may support streaming data to other components or user devices. Streaming caching storage 526 is a location where streaming data can be cached. For example, assume that component 418 is a piece of equipment operating at Location A and that a user using a computer in Location B desires to view a live of substantially live stream of outputs of the piece of equipment. Component 418 can send a portion of data to streaming caching storage 526 which can retain the portion of the data for a certain period of time (e.g., 1 day). Thus, streaming caching storage 526 is configured to cache data that can be streamed.

Diagram 500 also includes data store integrity engine 506. In some examples, data store integrity engine 506 is configured to ensure integrity of the information within data store 508. For example, data store integrity engine 506 applies one or more rules to decide whether information within all or part of data store 508 should be scrubbed, removed, or adjusted. In this manner, confidence is increased that the information within data store 508 is accurate and current.

Figure 6:
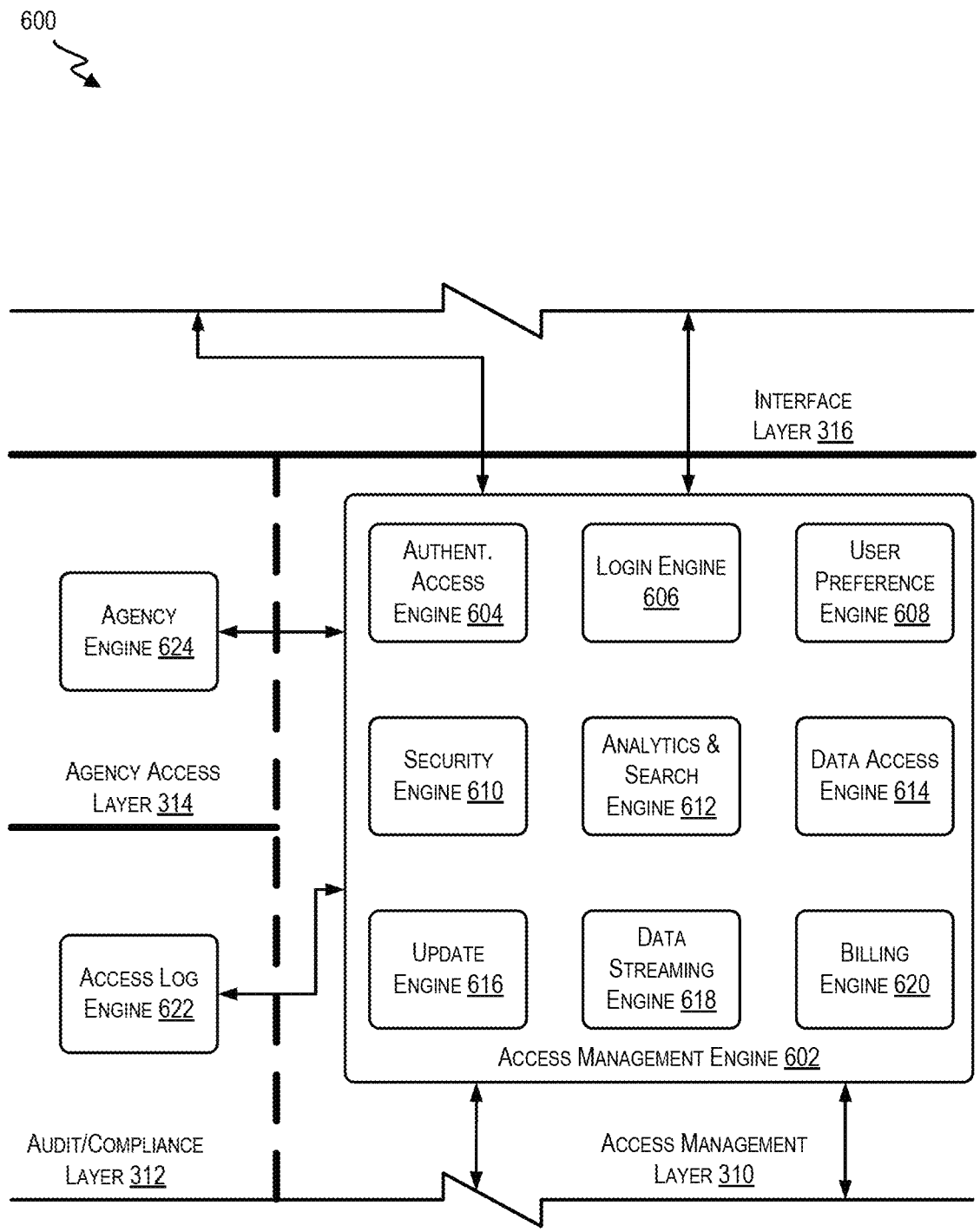
FIG. 6 is an example schematic model illustrating an aspect of the network communication model of FIG. 3 in more detail.

FIG. 6 shows a diagram 600 which depicts a portion of architecture stack 300 according to at least one example. In particular, the diagram 600 includes access management layer 310, audit/compliance layer 312, agency layer 314, and a portion of interface layer 316.

Access management layer 310, as illustrated in the diagram 600, includes an access management engine 602. Access management engine 602 is an example of access management engine 222. Generally, access management engine 602 can be configured to manage access to elements of transformative processing engine 202 by different components, applications, and user devices.

Access management engine 602 within access management layer 310 also provides functionality similar to an operating system. For example, access management engine 602 includes a plurality of engines configured to manage different aspects of interacting with elements of the interaction system. For example, a user who desires to access portions of data retained in data store 508, may do so by interacting with access management engine 602 using one or more applications (not shown). Thus, access management engine 602 includes a variety of engines to enable such interaction. The engines include, for example, an authentication access engine 604, a login engine 606, a user preference engine 608, a security engine 610, an analytics and search engine 612, a data access engine 614, an update engine 616, and a streaming data engine 618. The different engines of access management engine 602 can define routines, protocols, standards, and the like for interacting with elements of the interaction system.

Beginning first with authentication access engine 604, authentication access engine 604 evaluates the rules and conditions under which users may access elements of the interaction system; in particular, the conditions under which users may access data within data store 508. These rules and conditions may be user-defined (e.g., by an administrator or reviewer), learned over time, and/or may be dynamically updated and/or evaluated based on characteristics of the user or the user's device attempting to access the interaction system. The rules and conditions may indicate the types of users who have particular types of access within the interaction system. The type of access may also relate to the degree to which data is identified/de-identified. In some examples, a user desiring access to data provides certain identifying information and authentication access engine 604 authenticates an identity of the user.

Login engine 606 evaluates the rules and conditions under which users are able to log in to the interaction system or access applications associated with the interaction system. These rules and conditions may be user-defined (e.g., by an administrator), learned over time, and also may be dynamically updated and/or evaluated based on characteristics of the user or the user's device attempting to access the interaction system. Thus, while authentication access engine 604 evaluates the rules to determine which users may access the interaction system, login engine 606 evaluates the particular credentials, profiles, etc. of the users. For example, login engine 606 can confirm that an entered username (e.g., and password), provided biometric data or code or identifier in a scanned tag or badge matches that in an authorized user data structure.

Login engine 606 evaluates one or more user profiles associated with each authenticated user. In some examples, a user profile includes a username, password, and other information associated with the user. For example, a user profile may indicate characteristics about the user.

User preference engine 608 evaluates the rules and conditions under which user are able to store and update one or more user preferences corresponding to access of the interaction system or access to applications associated with the interaction system. These rules and conditions may be user-defined (e.g., by the user or administrator), and may include rules for default preferences. For example, using user preference engine 608, a user may indicate a format in which the user prefers to receive outputted information, display characteristics of a graphical user interface associated with the user, and other similar user preference settings. For example, the user may indicate that certain types of reports and/or alerts are to be sent to the user.

Security engine 610 evaluates the rules and conditions for ensuring the security of access to the elements of the interaction system. In some examples, these rules and conditions are determined by administrators of the interaction system. In some examples, security engine 610 provides a plurality of computer virus protection services. These services can be called up and implemented when accessing the interaction system or accessing applications associated with the interaction system. The rules and conditions may be based on roles, based on profiles, based on domains, and any other suitable security configuration. For example, because the interaction system may include sensitive data, security engine 610 may enforce a domain-based rule that protects certain sensitive information (e.g., identifying information).

Analytics and search engine 612 evaluates the rules and conditions under which users can search for data within the interaction system and access analytics relating to the interaction system. In some examples, these rules and conditions are user-defined or learned over time in accordance with search engine optimization techniques. For example, analytics and search engine 612 is used to search within data store 508 for particular data. Analytics and search engine 612 supports any conventional searching algorithms. For example, search engine 612 can be used to search within various fields and potential field values. In some examples, search engine 612 can provide analytics, such as statistics, graphs, distributions, and/or comparative analysis pertaining to particular entities and/or characteristics. Such information may be selected by a user and presented on a user interface.

Data access engine 614 evaluates the rules and conditions under which users may operation in order to access particular data within data store 508. In some examples, these rules and conditions are user-defined or learned over time. For example, data access engine 614 may indicate the routines, subroutines, or other logic needed for an application to access certain portions of data store 508. For example, while authentication access engine 604 and login engine 606 may manage which users can access parts of the interaction system, data access engine 614 may manage how authenticated users access data within data store 508. To this end, data access engine 614 may enforce and/or evaluate certain rules managing how users access different components of the interaction system. In some examples, data access engine 614 may be used to actually access data within data store 508 (e.g., extract, download, or otherwise access). In some examples, data access engine 614 may define procedures, protocols, and the like for accessing data. The protocols and procedures for accessing data access engine 614 (like the other engines of access management engine 602) may be provided to developers in the form of a software development kit (SDK). SDKs may enable developers write applications that can effectively communicate with elements (e.g., data store 508) of the interaction system. In particular, applications that can access a portion of the data stored within active unified data layer 308.

Update engine 616 evaluates the rules and conditions for providing updates to other engines within access management engine 602, plug-ins for applications that access the interaction system, and for other similar elements of the interaction system. For example, updates may be generated at runtimes, at defined time intervals, upon request by a user, upon receiving a threshold quantity of new or changed data. Once an update is performed, an interface may be refreshed, a report may be sent indicating that the update was successful or unsuccessful, or the like.

Streaming data engine 618 defines the rules and conditions for enabling streaming of data between components and user devices of the interaction system. For example, streaming data engine 618 may enable component 414 to stream data. Streamed data may include live or substantially live audio or video feeds, results of tests, output from equipment or devices, and any other suitable type of data capable of being streamed. In some examples, the data may be streamed to other components or user devices within the network or outside the network. In order to establish a streaming transmission, streaming data engine 618 may identify a streaming destination and a streaming origin. Next, streaming data engine 618 may pair the two and enable streaming. This may include allocated bandwidth within one or more network devices associated with the interaction system. Streaming data engine 618 may also adjust the quality of the streaming data based on the availability of bandwidth. In some examples, streaming data engine 618 may receive incoming streams (and continuously present the stream or monitor for particular data (e.g., exceeding a threshold, exhibiting an above-threshold change, having a particular value)).

Within audit/compliance layer 312 is located an access log engine 622. Access log engine 622 evaluates the rules and conditions for logging access to the interaction system by users, applications, devices, and the like. Logging access includes, in some examples, logging data conventionally collected by access log engines running in similar environments. Access log engine 622 can use this data to generate and transmit reports, for example, to stakeholders of the interaction system such that they can make informed decisions regarding that is accessing the interaction system and for what purposes.

Within agency layer 314 is located an agency engine 624. Agency engine 624 evaluates the rules and conditions under which agencies can access the interaction system. In some examples, agency engine 624 may be used to track one or more performance indicators identified by a government agency and/or to provide report instances of defined types of events. In some examples, a university is an agency that uses agency engine 624 to collect data pertaining to one or more studies. Agency engine 624 can collect the pertinent data, potentially format and/or analyze the data, and facilitate transmission of the data to the appropriate agency.

Figure 7:
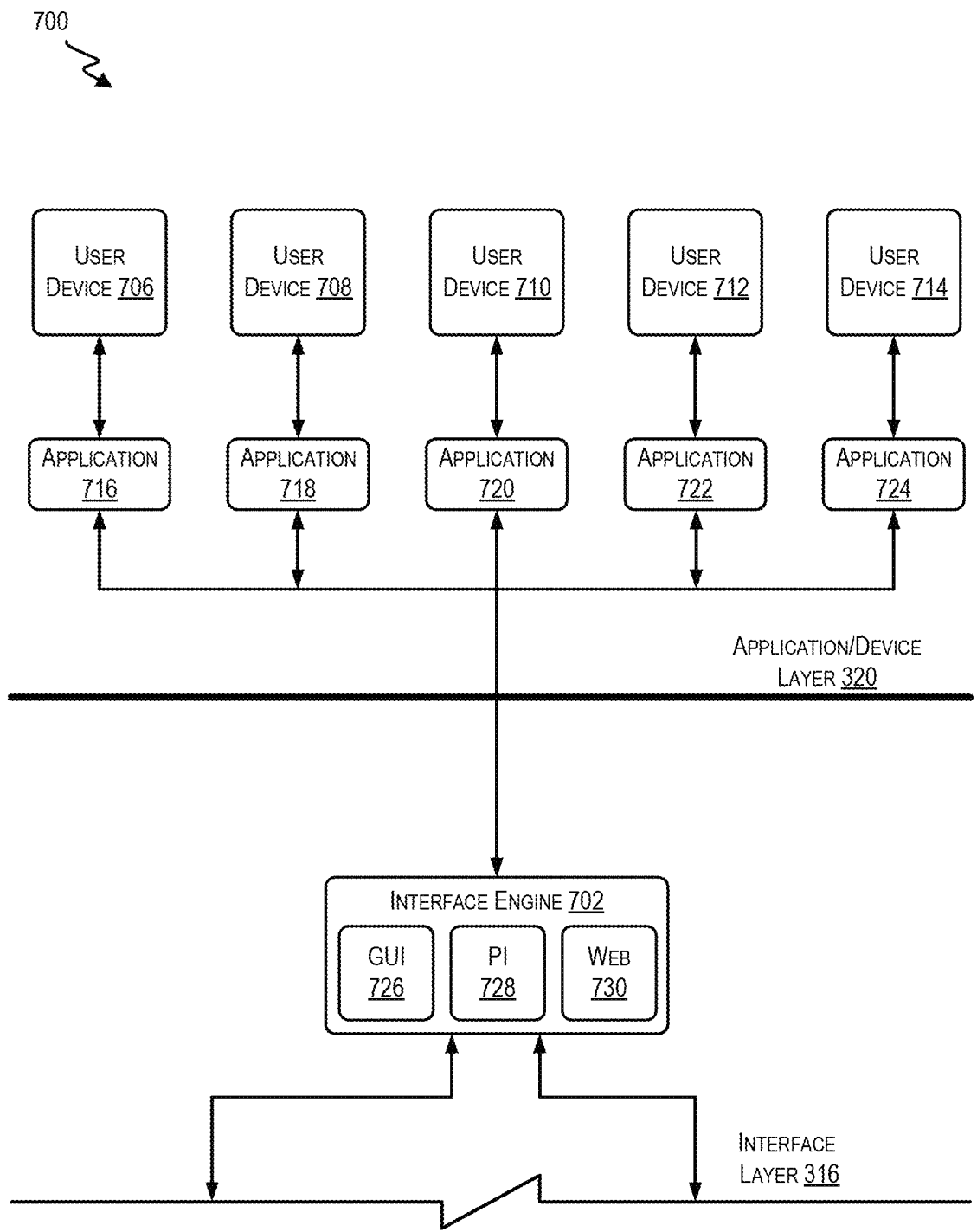
FIG. 7 is an example schematic model illustrating an aspect of the network communication model of FIG. 3 in more detail.

FIG. 7 shows a diagram 700 which depicts a portion of architecture stack 300 according to at least one example. In particular, diagram 700 includes interface layer 316, and application/device layer 320. Within interface layer 316 is located interface engine 702 (e.g., interface engine 224). Interface engine 702 is configured to generate one or more interfaces (e.g., graphical user interface 726, programmatic interface 728, and/or web interface 730) to enable data to flow to user devices 710, 712, and 714 via respective applications 720, 722, and 724. In some examples, the interfaces of interface engine 702 are embodied in hardware, software, or some combination of both. Within interface layer 316 communications and inputs directed to interacting with elements of access management layer 310 may be embodied.

Graphical user interface 726 is any suitable graphical user interface configured to interact with elements of the interaction system. Programmatic interface 728 includes an application programming interface, a programmatic user interface, and other similar interfaces for defining core functions for accessing elements of the interaction system. For example, programmatic interface 728 may specify software components in terms of their operations. Web interface 730 is any suitable web interface configured to interact with elements of the interaction system. Any of the interfaces described herein may be configured to receive user input, present dynamic presentations that depend on user input, and otherwise respond to user input. In some examples, such input may be provided via one or more input devices (e.g., a keyboard, touchscreen, joystick, mouse, microphone, devices capable of capturing inputs, and the like) operated by one or more users of user devices 706-714. Output may be provided via one or more output devices (e.g., a display or speaker).

Interface engine 702 is utilized by applications internal to the interaction system and external to the interaction system to access data. In some examples, the applications that are internal include applications that are developed for internal use by various entities associated with the interaction system. In some examples, the applications that are external to the interaction system include applications that are developed for external use by those that are not associated with the interaction system.

Generally, within application/device layer 320, applications 716-724 which communicate with other elements of architecture stack 300 using the interfaces generated by interface engine 702 are defined. This includes detailing how applications 716-724 are to interact with the interfaces generated by interface engine 702 for accessing data. For example, interacting may include accepting inputs at user devices 706-714 to access data and, in response, providing the data, prompts, or other types of interaction with one or more users of the user devices 706-714. Thus, applications 716-724 may be related to one or more of the interfaces generated by interface engine 702. For example, application 720 may be interact with a graphical user interface (whether generated by interface engine 702 or otherwise) to interact with other elements of the interaction system. Interacting may include receiving inputs at the graphical user interface via application 720, providing output data to the graphical user interface application 720, enabling interaction with other user devices, other applications, and other elements of the interaction system, and the like. For example, some of the inputs may pertain to aggregation of data. These inputs may include, for example, types of data to aggregate, aggregation parameters, filters of interested data, keywords of interested data, selections of particular data, inputs relating to presentation of the data on the graphical user interface, and the like. Providing output data may include providing the aggregated data on the graphical user interface, outputting the information to one of the other user devices 706-714 running one of the other applications 716-724.

Turning now to the details of applications 720, 722, and 724. In some examples, applications 720, 722, and 724 include a variety of different applications that can be designed for particular users and/or uses. In one example, application 720 includes dashboards, widgets, windows, icons, and the like that are customized for a particular entity. In some examples, application 720 may present different data depending on a focus of the entity and protected information associated with the entity. In this manner, application 720 adapts and automatically adjusts depending on the context in which the entity is using the application. Application 720 may be configured to receive input, adjust presentations, present unprompted alerts, adjust display of content, move more relevant content to the foreground, move less relevant content to the background, and/or populate forms for the entity.

In another example, application 722 may be specific for nurses or types of nurses. In this example, application 722 may include dashboards, widgets, windows, icons, and the like that are customized to individual nurses. Similar to the example discussed above pertaining to the user, in some examples, application 724 may present different data depending on a position of the nurse. In this manner, application 722 adapts and automatically adjusts depending on the context in which the nurse is using the application. For example, the nurse may receive data, such as test results.

In some examples, application 724 may be a multi-role application for administrators and is used to manage entities constitute the population of the entities or organizations within the interaction system. Similar to the other examples discussed, in some examples, application 724 may present different data depending on a role of the user who is using application 724. In this manner, application 724 adapts and automatically adjusts depending on characteristics of the user who is using application 724. In this manner, application 724 can provide different data depending on the role of the user. For example, whether data presented includes identifiable or de-identified information may depend on a position of the user.

Applications 716 and 718 shown in connection with interface engine 702 are applications developed by third-parties. In some examples, such applications include any suitable application that benefits from accessing data. The interaction system may include data pertaining to hundreds of thousands of entities. Having data pertaining to so many entities presents security concerns. For example, much of the data may be identifying data. Accordingly, data that may be accessed by applications 716 and 718 may be limited. In some examples, an entity of the interaction system may use one of applications 716, 718 to access his or her own data. In this example, the identity of the entity may be verified in accordance with techniques described herein.

User devices 706-714 are any suitable user devices capable of running applications 716-724. User devices 706-714 are examples of the user device 228. In some examples, the user devices include: mobile phones, tablet computers, laptop computers, wearable mobile devices, desktop computers, set-top boxes, pagers, and other similar user devices. In some examples, at least some of user devices 706-714 are the same devices as at least some of the one or more components 410-418. In some examples, user devices 706-714 may include complementary layers to application/device layer 320 and/or receiving layer 302. For example, user devices 706-714 may include a transmission layer, a generation layer, and/or a receiving layer to communicate data at application/device layer 320 and at receiving layer 302.

Figure 8:
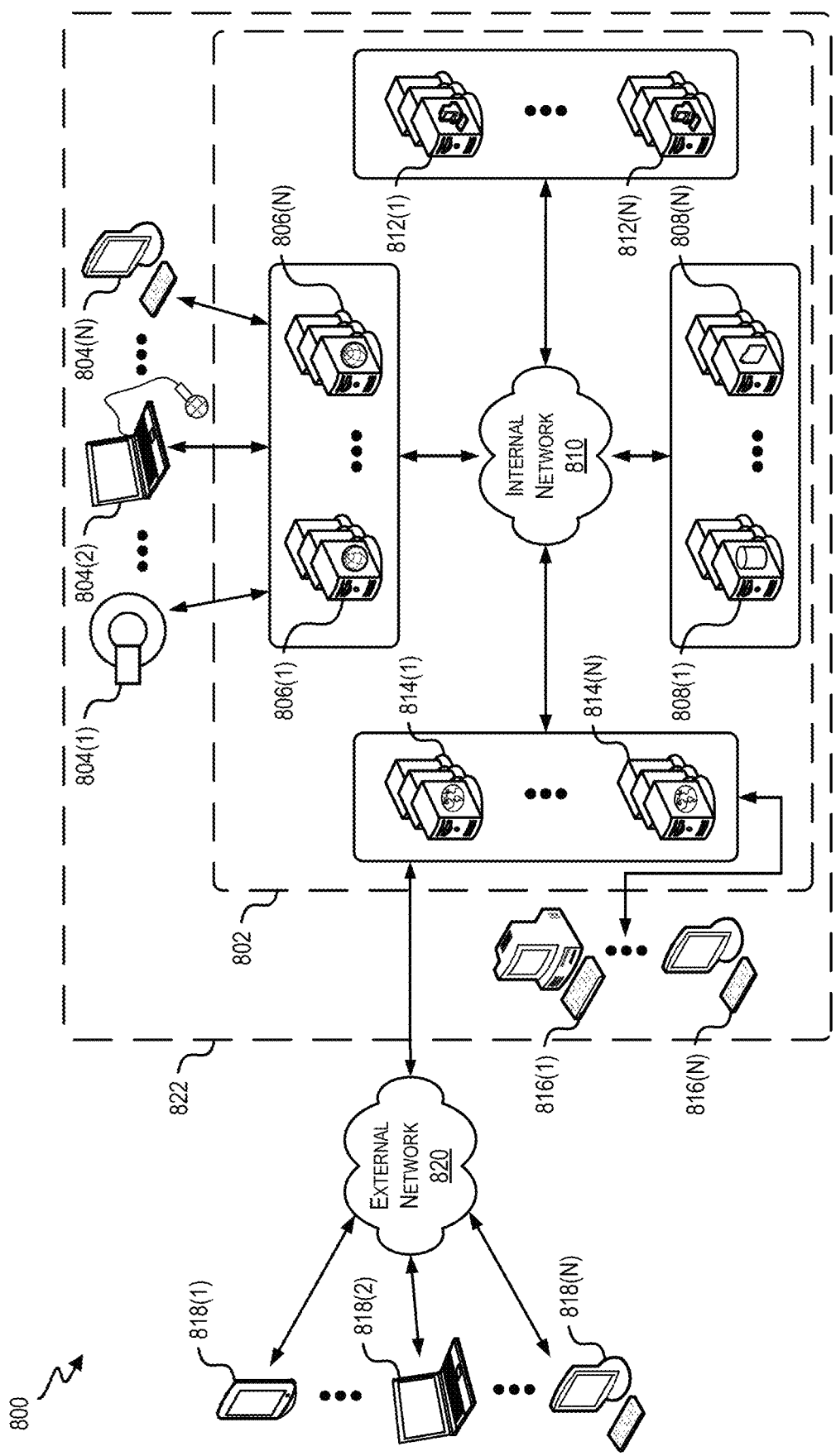
FIG. 8 is an example schematic architecture illustrating an interaction system in which techniques relating to providing a probability score that a user will be readmitted to a unit may be implemented, according to at least one example.

Turning now to FIG. 8, an interaction system 800 is shown according to at least one example. Interaction system 800 includes an internal organization 822 including a transformative processing engine 802. The transformative processing engine 802 is an example of transformative processing engine 202 previously discussed. Interaction system 800 is illustrated as an example configuration for implementing the techniques described herein. In particular, a configuration of elements as illustrated in FIG. 8, at least in some examples, communicates according to the layers of architecture stack 300. For example, internal organization 822 includes generation components 804(1), 804(2), and 804(N) which provide data to aggregation servers 806(1)-806(N).

Generation components 804(1), 804(2), and 804(N) operate in accordance with receiving layer 302. In some examples, generation component 804(1) is a piece of equipment, generation component 804(2) is computer with a data collection device, a type of lab system, and generation component 804(N) is a terminal. Aggregation servers 806 (1)-806(N) operate in accordance with aggregation layer 304. Aggregation servers 806(1)-806(N) share data with data storage servers 808(1)-808(N) via one or more internal network(s) 810. In some examples, internal network 810 is any suitable network capable of handling transmission of data. For example, internal network 810 may be any suitable combination of wired or wireless networks. In some examples, internal network 810 may include one or more secure networks. Data storage servers 808(1)-808(N) are configured to store data in accordance with active unified data layer 308. Data storage servers 808(1)-808(N) include database servers, file storage servers, and other similar data storage servers.

Access management servers 812(1)-812(N) manage access to the data retained in the data storage servers 808(1)-808(N). Access management servers 812(1)-812(N) communicate with the other elements of interaction system 800 via internal network 810 and in accordance with access management layer 310.

Interface servers 814(1)-814(N) provide one or more interfaces applications to interact with the other elements of interaction system 800. Interface servers 814(1)-814(N) provide the one or more interfaces and communicate with the other elements of interaction system 800 via internal network 810 and in accordance with interface layer 316. The interfaces generated by the interface servers 814(1)-814(N) can be used by internal user devices 816(1)-816(N) and external user devices 818(1), 818(2), and 818(N) to interact with elements of interaction system 800.

Internal user devices 816(1)-816(N) are examples of user devices 706-714. In some examples, internal user devices 816(1)-816(N) run applications via the interfaces generated by interface servers 814(1)-814(N). As an additional example, external user devices 818(1), 818(2), and 818(N) can run applications developed by third parties that access the other elements of interaction system 800 via the interfaces generated by interface servers 814(1)-814(N).

External user devices 818(1), 818(2), and 818(N) access the interfaces via external network 820. In some examples, external network 820 is an unsecured network such as the Internet. External user devices 818(1), 818(2), and 818(N) are examples of user devices 706-714. External user device 818(1) is a mobile device. In some examples, the mobile device may be configured to run an application to access interaction system 800. Similarly, the other external user devices 818(2)-818(N) run applications that enable them to access interaction system 800. While interaction system 800 is shown as implemented using discrete servers, it is understood that it may be implemented using virtual computing resources and/or in a web-based environment.

The systems, processes, and models described with reference to FIGS. 1-8 may be used to implement the techniques described herein with reference to later figures. For example, data communication may be performed within the aggregation layer 304 or the active unified data layer 308. In some examples, messages originate at one of the components 410-418 and are streamed to the data store 508. These messages may be intercepted by the collection engine 504 or any other suitable interceptor device and shared with prediction system described herein.

Additionally, the prediction system may be implemented using elements of the systems, networks, and models of FIGS. 1-8. For example, the prediction architecture may include the transformative processing engine 202. The transformative processing engine 202 may process data used by a prediction system and store/retrieve the data to/from the data store 508 (e.g., the data store 226).

Examples described herein provide different systems and methods for supporting a user service coordinator (UC) in the process of coordinating user service. The systems and methods provided are suitable to support a UC in a variety of environments and contexts. For example, some environments may involve coordinating user service across an entire enterprise, while another environment involves coordinating service among users in a single unit (e.g., a service center or service facility), or a division of the enterprise that contains multiple service units. In another example of a particular context, the system might be helping the UC coordinate service among all users of a service facility, while another context may be focused on a particular category of user (e.g., users who fall under a particular type of service(s) and/or may fall under a bundled payment model). In yet another example, the system may assist a UC in coordinating user service while a user is still admitted and being serviced for a reported issue in a service facility. In yet another context, the UC may be coordinating user service that is targeting post-release. In some contexts, the system may assist a UC in coordinating user service among other service providers (e.g., post-release), while in other contexts the system may improve the process of allowing users to contact a UC and receive service advice post-release. These various environments and contexts will be discussed herein below.

In one example, a prediction system provides support for a user coordinator (UC) that is coordinating service for users within a service system. The service system (e.g., which also may be known as the "enterprise") may include a plurality of divisions, and each division may include one or more service facilities. For example, the enterprise may geographically organized within the United States (U.S.), whereby there is a division per state, county, or the like. Each division may include several service facilities (e.g., service units, labs, rehabilitation centers, home service agencies, and any other user service center where a user may receive service by a service provider). The UC may be an administrator of the enterprise (e.g., at an enterprise level, division level, or service facility level). In some cases, the UC may also be a service provider, or other service professional. Typically, a service facility will admit a user for a particular reported issue, and the user may receive service for the reported issue for a period of time, after which time the user is released. In some cases, after being released, a user may require further service to service the original reported issue and/or may be readmitted to one of the service facilities of the enterprise. To help coordinate service among service facilities of the enterprise, improve user service results, and improve efficiencies of providing user service, the prediction system may provide support to a UC in several different forms and using various methods. For example, the prediction system may provide a prediction to a user device of a UC that corresponds to a particular user that is currently admitted to be serviced for a reported issue within a service facility. As referenced herein, depending on the context (e.g., the use of a threshold value), a "prediction" may be used interchangeably with a "probability score", and may predict the likelihood that the user will be readmitted to one of the service facilities of the enterprise (or the division) within a pre-defined post-release time period (e.g., 90 days) that follows a date of release of the user from the present admission. For example, in some cases, the prediction may be a prediction that is based on whether or not a probability score matches a threshold value (e.g., Probability Score: 40%; Threshold value: 50%; Prediction: "User likely won't require readmission"). In other cases, the prediction may be in the form of a direct probability score (e.g., Prediction: 40% chance of readmission). The prediction system may generate a probability score by utilizing an artificial intelligence (AI) model (e.g., a "machine learning" (ML) model). The ML model may be trained according to one or more training features, whereby each training feature may be determined based on its ability to predict the likelihood that the user may be readmitted for the current issue within the pre-defined post-release time period. The ML model may be trained based on data elements from user service records (USR) from one or more facilities of the enterprise, the data elements each corresponding to one or more training features. Once the ML model has been trained, and returning to the example above, the trained ML model may receive as input data elements from the current user's service record, and output the probability score. The probability score may then be displayed on a user device of the UC, to be used to coordinate service. For example, if the probability score matches (e.g., equals or exceeds) a certain pre-defined threshold value, the UC may determine that the user is a good candidate for coordinated service. This coordinated service may be in the form of regular follow up calls from a service provider, email reminders to the user to follow a prescribed service plan, and the like.

To provide a higher rate of predictive accuracy for a given probability score output by a ML model of the prediction system, the prediction system may employ one or more ML models. These ML models may be combined together using one or more mechanisms in order to provide a higher prediction accuracy. In an example, a first ML model may be trained using training data drawn from user service records across the entire enterprise. This may provide a broad sampling of training data to help avoid overfitting and/or overfitting of data. Meanwhile, a second ML model, may be trained using only a portion of the user service records of the enterprise (e.g., focusing on a particular division). By training the second ML model using only training data from the particular division, the second ML model may be better configured to predict user service results for users in that specific geographic region. The first ML model and the second ML model may be combined together using one or more mechanisms. For example, the output of the first ML model may be used as an input to the second ML model, or vice versa. In another example, both ML models each output a respective probability score, and then the respective probability scores may be combined according to an algorithm (e.g., weighted average). It should be understood that the use of multiple ML models may be employed at various levels. For example, instead of (or in addition to) training a first ML model at the enterprise level, the first ML model may be trained at the division level. Meanwhile, a second ML model may be trained at a per-service facility level. The two or more ML models may be combined using any suitable mechanism, for example, as described above. By training an ML model at a lower (e.g., per service facility) level, the ML model may be better attuned to characteristics (e.g., user demographics, financial data, geographical considerations) of a particular service facility.

In another example, a prediction system may assist a UC by predicting if the issue of a user will be analyzed as belonging to one of a predefined set of service groups. If the user is predicted to fall in one of the predefined set of service groups, the prediction system may further predict which particular service group of the predefined set of service groups the issue of the user will most likely be categorized under. For additional context, a service group may correspond with one or more service group codes. A service group code may correspond to a particular analysis result or issue of a user, which in turn may correspond to a particular product and/or service received by the user for that particular issue. As an example, the Centers for Medicare and Medicaid Services (CMS) may maintain a list of service group codes (e.g., Medicare Severity-DRGs (MS-DRGs (diagnosis-related groups)) which are used to determine whether a user qualifies to be under a particular bundled payment model. Under a bundled payment model, CMS service providers and/or service facilities are paid a single payment for all the services performed to service a user undergoing a specific episode of service. An episode of service is the service delivery process for a certain issue or service delivered within a defined period of time. For example, a user may be admitted to a service unit for a particular issue (e.g., a hip injury). The user issue may be analyzed and the particular service plan may be categorized as corresponding to a particular service group code (e.g., MS-DRG 466), which may correspond to a hip replacement revision surgery. In this example, the particular MS-DRG code 466 may belong to the service group for Hip or Knee Replacement Revision (e.g., which may include codes 466, 467, and 468) that is maintained by the CMS. Because the user was analyzed under this particular service group code and/or family, the user may qualify to fall under a bundled payment model that is applicable to the particular service facility where the user first received service (e.g., hip surgery). As such, even though after the surgery, the user may require follow up service (e.g., physical therapy, check-up appointments, medication, etc.), the CMS may pay the service facility a single payment for the episode of service (e.g., to service the user for the hip injury), which covers both the initial admission and service, as well as follow up service within a predefined period of time (e.g., determined by the CMS to be 90 days). Service providers under this bundled payment model therefore have incentive both financially to improve cost efficiencies and improve overall customer user service. This translates to an incentive to improve user data gathering, analysis, and outcome prediction techniques. For example, service providers may want to predict what a user's needs may be throughout an episode of service, so that the service provider can coordinate with the appropriate parties early on to provide the optimal user service. Returning to the prediction system capabilities described above, the prediction system may predict, using a first ML model, the probability that a user's issue may fall into any one of a set of service groups. In an example, these service groups may form a set of service groups for which a service facility servicing the user is contracted with the CMS to be participating in a bundled payment model. The first ML model may be further configured to compare the outputted probability value with a threshold value that is predetermined by the UC. If the outputted probability value matches (e.g., equals or exceeds) the threshold value, the prediction system may determine that the user will likely qualify to be in a service group, and, in turn, input user data into a second ML model. The second ML model of the prediction system may predict which particular service group the user may be categorized under. The prediction system may then display this data to the UC for further action. In an example, the UC, upon receiving information indicating a strong likelihood that the user will be categorized under a particular service group that qualifies for a bundled payment model, may set a reminder to contact the user after release to ensure that the user understands and follows the service plan for their issue. In another example, the UC may communicate to downstream service providers (e.g., physical therapist, nursing staff) to follow up with the user. In this way, the prediction system enables improved overall coordinated user service while also improving service efficiencies.

In another example, the prediction system may provide user outcome data from one or more service facilities of the enterprise to be displayed in a uniform dashboard on a user device. For example, a first service facility of the enterprise may be associated with a first ML model and a second ML model. Both of these models may be trained similar to the previous example, for example, respectively outputting: (1) a probability that a user analysis result will correspond to a service group of a set of qualifying service groups (e.g., a binomial classification), and (2) if the first probability matches a predetermined first threshold value, then outputting a probability that the user analysis result will correspond to a particular service group of the set of qualifying service groups (e.g., a multi-categorical classification). Both the first and second ML models may be trained using training data that is specifically suited for first service facility (e.g., drawing predominantly from user data from the first service facility). Also, the first threshold value may be chosen specifically customized for the first service facility. For example, as discussed above, the first threshold value may set a threshold which determines whether the prediction system classifies a user as belonging to a set of qualifying service groups or not (also may be known as a "qualifying user"). In setting the threshold value, a UC may take into account an acceptable error rate (e.g. false positives, false negatives). In other words, the UC may determine the threshold value in light of whatever error rate is tolerable by the first service facility as well as whatever percentage of the actual total number of qualifying users the first service facility aims to capture. It should thus be understood that the first and second ML models (e.g., including the training data used to train the models) and additional configuration settings and policies (e.g., threshold value, desired capture rate, acceptable error rate, etc.) may be specific to a particular service facility. For example, a second service facility of the enterprise may have a similar setup as the first service facility, being training and configured with data that is unique to the second service facility. A UC of the enterprise may be interested to view prediction data that is presented in a uniform manner across different service facilities in a division (e.g., the first and second service facilities), or even the entire enterprise. Accordingly, the prediction system provides a list of data, retrieved from prediction data of a plurality of service facilities, to be displayed on a dashboard of a user device of the UC. In this way, for example, the UC may compare prediction statistics across different service facilities, determine how best to allocate resources between facilities of the enterprise, determine if a ML model of a particular facility needs to be re-trained, etc.

In another example, a prediction system may utilize a combination of probability scores from different ML models to assist a UC in determining whether a particular class of user is a good candidate for user service coordination. For example, a prediction system of a service facility may employ two ML models. A first ML model may be trained to receive as input one or more data elements of a USR, and output a probability that the user will be readmitted for service to another service facility in the enterprise within a predetermined period (e.g., 90 days). A second ML model may be trained to receive one or more data elements of the USR (which may be the same or different data elements of the USR than the first model), and output a probability that the service group code determined for the user will qualify the user to fall under a bundled payment model. The prediction system may determine, based on the output from the first and second ML models, a final probability score that corresponds to a likelihood that the user is a candidate to receive user service coordination. In an example, the prediction system multiplies the output from the first and second ML models to produce the final probability score. The final probability score (and potentially the other scores) are provided to a user device of the UC for presentation on the user device. In an example, the user device may, based on the final probability score matching a certain threshold value, prompt the UC to take further action specific to the user. This action may involve developing a service plan that involves regular follow up calls to the user. The UC may provide a telephone number to the user for the user to text (or call) whenever the user needs service assistance. Upon receiving a text (or call), the UC may immediately know which user is requesting assistance, and provide immediate assistance (e.g., service recommendation) that is tailored to the user's needs. Other follow up actions may be suitable as appropriate.

Building from the previous example, prediction system, upon determining that a user should be classified as being a candidate for user service coordination, may cause the user to be provisioned with a user input device. In an example, the user input device may be a button (e.g., implemented in hardware or software), whereby the user may press the button at any time. Upon pressing the button, a signal is sent to a user device of the UC which alerts the UC that the user is requesting assistance. The prediction system may subsequently retrieve information about the user, and potential service recommendations, to be displayed on the user device of the UC. The UC may then contact that user to provide assistance, based on one or more of the potential service recommendations. The input device may not only provide for tactile input (e.g., pressing a button) by the user, but may also be configured to receive, for example, voice input (e.g., using Siri on an Apple device, Alexa on an Amazon device, etc.).

The present disclosure provides several advantages over existing solutions. As described above, it is important for a service provider to know, as early as possible, whether a user may require a specific service coordination. This service coordination may begin even while the user is still in a service unit being serviced for a particular issue. For example, based on the probability scores output by the one or more ML models, the UC may alert service providers in advance that the user will require special service, and process urgent paperwork in a timely fashion. The service coordination may continue when the user is released from a present admission. In this case, even though the user is not present in a service facility, the original service facility may want to keep in close contact with the user to ensure that they are following their service plan and that the service facility is quickly alerted to any change in the user's issue. In this way, the service facility can address problems early on, before they may become more difficult to service. The present disclosure also provides a centralized system and uniform method (e.g., presentation on a dashboard) for a UC to track predicted user service results across an enterprise. This is useful for determining how best to allocate resources across a large enterprise with many different service facilities. It also helps to indicate which service facilities may need to have improved prediction ML models, to ensure a consistent quality of user outcome prediction throughout the enterprise, which in turn improves user service across the enterprise. The present disclosure also provides an improved mechanism for coordinating service across multiple service programs. For example, a user service plan may involve interaction with multiple service providers (e.g., follow-up visit, lab work, therapy, etc.). Instead of having each service provider contact the user separately and uncoordinated, which may be overwhelming for a user to keep track of, the present disclosure provides a uniform method and centralized system for communicating with the user. For example, the service facility may provision a user device of the user with a software application, based on whether a user's prediction qualifies the user to receive coordinated service. The software application may be automatically connected with the relevant service providers and with the UC. Furthermore, upon receiving user input (e.g., pressing a button), the application may contact the UC and alert them that the user requires assistance. Based at least on previous data analysis by the prediction system, the UC may be presented with a list of potential recommendations for the user, which takes into account each of the past/future interactions with the multiple service providers involved in the user's service plan.

The advantages described above also enable several technical advantages that improve the functioning of the computer system in which the prediction system is implemented. For example, by providing a prediction of a user's outcome early in the process to enable a UC to take appropriate action (including coordinating with other service providers), the techniques described herein may reduce the total number of messages that are required to be processed by a service provider system to coordinate user service. By reducing the total number of messages required per user, multiplied over a large number of users in a service system, this may improve network efficiency (e.g., increasing available bandwidth) and increase computing resources available to the computer system. This may also lead to improved memory utilization because the number of messages required for processing and storage is reduced. Additionally, because the systems and predictive models are trained using the largest and most relevant datasets available (i.e., those maintained in one of the world's largest user data warehouses), the predictions made using the described system are more precise and more accurate than those made by prior art systems trained using smaller datasets. Additionally, because of the quality of the models, fewer computing resources are required to make the predictions as would be required using the prior art systems.

Another technical advantage relates to providing a centralized system for performing the techniques described herein. For example, by implementing the techniques described herein on a centralized server, processing capabilities are freed up on local computing devices (e.g., service facility endpoints). For example, while ML models may be trained to take into account each service facility's unique features, the actual training of the ML models and regular generation of user outcome prediction reports may be done on a centralized server across the entire enterprise. This enables increased computing efficiency in training the models and generating the reports, as well as ensuring that the reports are output in a consistent and timely manner. Based on these technical advantages and others described further below, the prediction system enables an enterprise (especially a large scale enterprise with many service facilities and service providers) to provide better coordinated service for users, to achieve better user service results, and to improve service efficiencies.

Figure 9:
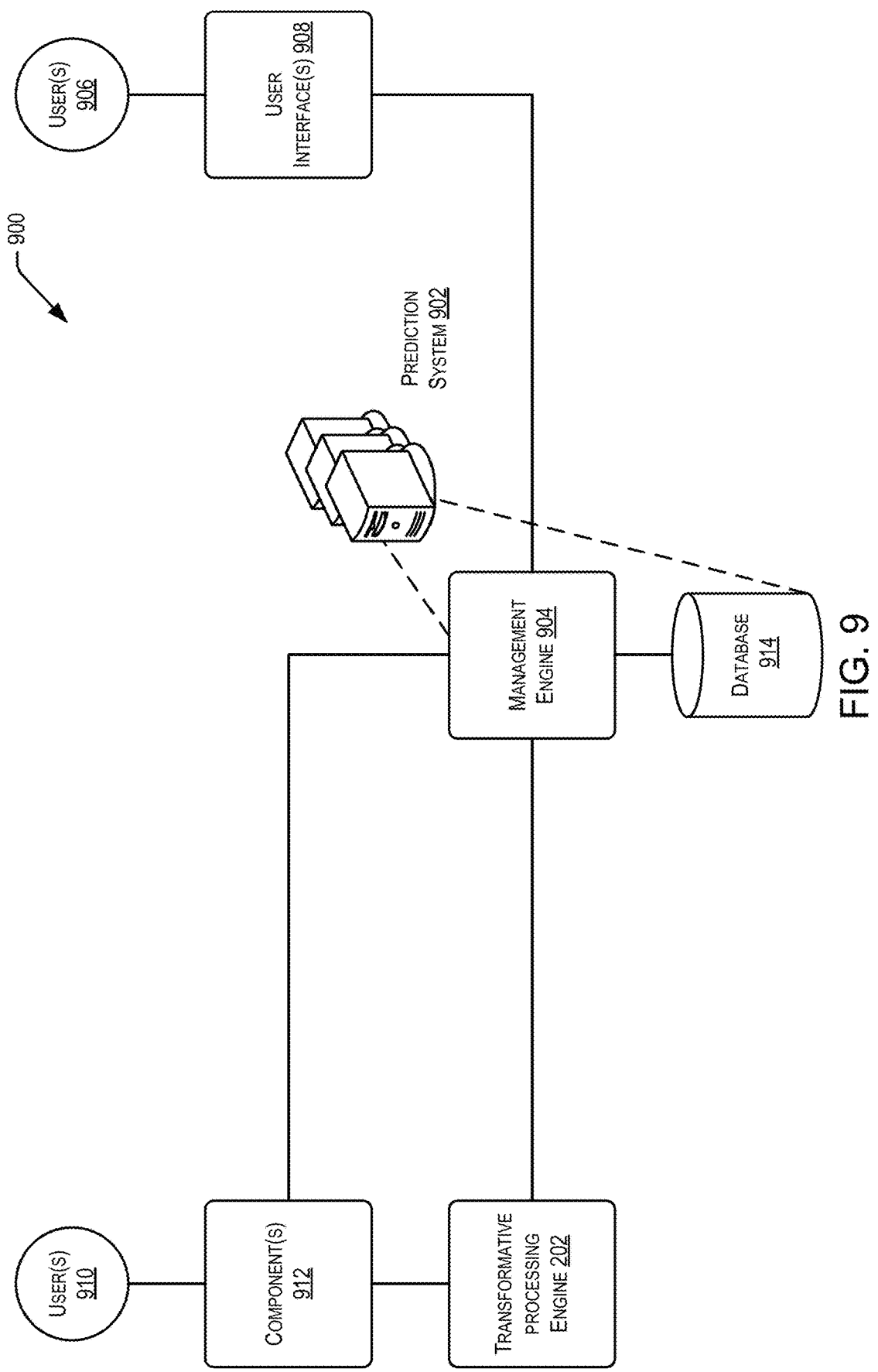
FIG. 9 is an example architecture illustrating a system in which techniques relating to providing a probability score that a user will be readmitted to a unit may be implemented, according to at least one example.

Turning now to FIG. 9, a prediction architecture 900 is shown, in accordance with at least one example. The prediction architecture 900 may be implemented using elements of the systems, networks, and models of FIGS. 1-8. For example, the prediction architecture 900 includes the transformative processing engine 202, which is described in detail herein. The transformative processing engine 202 can process and store data used by a prediction system 902 to implement the techniques described herein. For example, the prediction system 902, which includes a management engine 904, can access user data, which may include a user service record, interaction data (e.g., between the user and the service provider), feedback data, outcome data, and the like from the transformative processing engine 202 and use such data to generate user outcome predictions (prediction) for a UC. For example, the prediction system 902 may utilize user data to train one or more artificial intelligence (AI) models (e.g., machine learning (ML) model), and as input to a trained AI model to generate one or more predictions. Predictions are provided to receiving users 906 (e.g., a UC, other service providers, or users) via one of more user interfaces 908. The user interfaces 908 may enable presentation of, and interaction with, predictions at user devices such as those described herein.

In order to generate predictions, the prediction system 902 may access user data, including information about an issue and/or user, which may include both historical service data and present service data about a present issue. The user data may also include information about interaction with the service provider, provider details, and other information that is related to the user service. The creation of information about the issue and/or user begins with generation users 910, which may include authorized users, UCs, administrators, and other service providers. The generation users 910 and the receiving users 906 may come from the same group of users and may be similar to the users that operate the components 410-418 and/or the users that operate the user devices 706-714. Accordingly, the generation users 910 interact with components 912 to generate service-related data (e.g., issue information about the issue and/or user). The components 912 are examples of the components 410-418 discussed herein.

The service-related data generated by the users 910 interacting with the components 912 is provided to the transformative processing engine 202 and the transformative processing engine 202 performs one or more operations on the service-related data such as those discussed herein. One of the operations includes the transformative processing engine 202 retaining the service-related data in a manner that makes it searchable and useable by other elements of the prediction architecture 900.

The prediction system 902 also includes a database 914. The database 914 is accessible by the management engine 904. The database 914 is used to store data about users and AI models of the prediction system 902. For example, the user data may include training data and testing data (e.g., to test the AI models). The database 914 can be distributed or otherwise made available to multiple users. In some examples, the database 914 may be centralized. In other examples, the database 914 may be decentralized (e.g., a database per division or per service facility). In some examples, the database 914 may store multiple AI models. It should be understood that, although in the embodiments described herein, multiple types of AI models may be described, the functions performed by the one or more AI models may also be performed within a single AI model or any suitable combination of models. The AI models, as described herein, can be initialized using data mined from the data store of the transformative processing engine 202. In some examples, data used to train the AI models is copied from the data store of the transformative processing engine 202 and stored within the database 914.

FIGS. 10, 11, 13, and 19 illustrate example flow diagrams showing respective processes 1000, 1100, 1300, and 1900, as described herein. These processes are illustrated as logical flow diagrams, each operation of which represents a sequence of operations that can be implemented in hardware, computer instructions, or a combination thereof. In the context of computer instructions, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described operations can be omitted or combined in any order and/or in parallel to implement the processes.

Additionally, some, any, or all of the processes may be performed under the control of one or more computer systems configured with executable instructions and may be implemented as code (e.g., executable instructions, one or more computer programs, or one or more applications) executing collectively on one or more processors, by hardware, or combinations thereof. As noted above, the code may be stored on a computer-readable storage medium, for example, in the form of a computer program comprising a plurality of instructions executable by one or more processors. The computer-readable storage medium is non-transitory.

Figure 10:
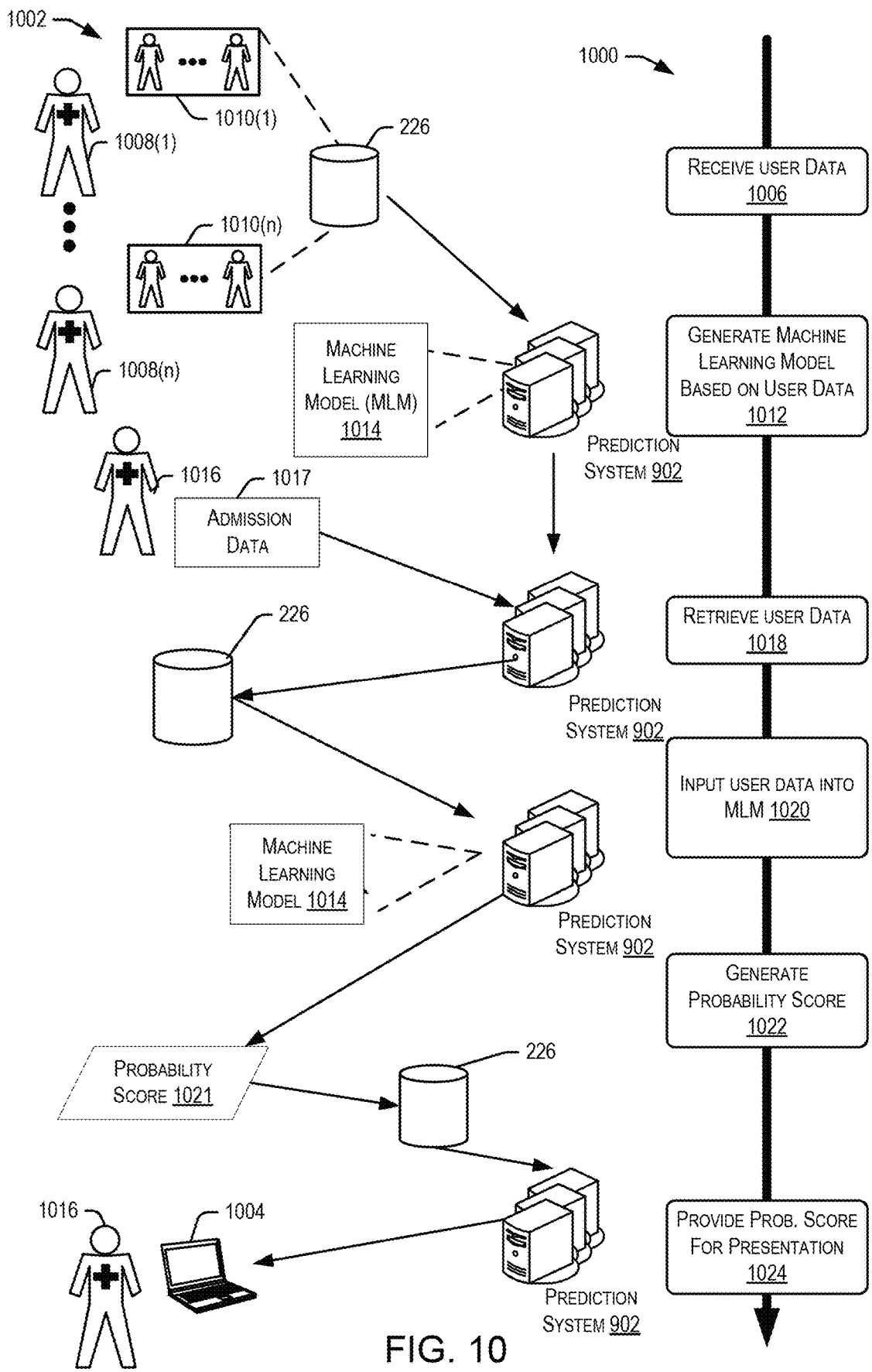
FIG. 10 is an example flowchart illustrating a process for providing a probability score that a user will be readmitted to a unit, according to at least one example.

FIG. 10 illustrates a simplified block diagram 1002 depicting an example process 1000, in accordance with at least one example. The process 1000 is an example process for generating a prediction using a trained AI model. The diagram 1002 depicts example states that correspond to the blocks of the process 1000. The diagram 1002 includes the prediction system 902, the data store 226 of the transformative processing engine 202, and a user device 1004 that perform at least a portion of the process 1000.

The process 1000 begins at 1006 by receiving user data. The user data may be used to generate user training data, discussed further below. The user data may be input by multiple providers 1008(1)-1008(n) within the enterprise, for example, with each provider corresponding to a representative for a particular service facility. In an example, a user device of each provider may receive the user data and transmit the user data over a network to the prediction system 902. It should be understood that in this context, a "provider" may be a service provider, a UC, an administrator, an authorized user, or any other suitable service professional. The user data can include data that was previously collected by the transformative processing engine 202 and stored in the data store 226. The user data includes data collected by multiple providers 1008(1)-1008(n) who interacted with or are responsible for sets of users 1010(1)-1010(n). For example, users 1010(1) may correspond to one or more users for a particular service facility, whereby the service facility is represented by provider 1008(1). In another example, users 1010(1) may correspond to all of the selected users for a particular division (each division having one or more service units), whereby the division is represented by provider 1008(1).

In some examples, the user data may identify characteristics of the user, diagnoses made by the providers 1008, associated service plans made by the providers 1008, associated service results of the users 1010 based on those service plans, and other suitable information. In some examples, the user data may indicate not only historical service data, corresponding to previous admissions of the user, but may also include present admission data, corresponding to a present admission of the user for an issue. The user data may also include data sets describing an expected or desirable course of service based on an issue. Table 1 below describes examples of user data that may be collected by the prediction system 902. It should be understood that some of the user data element examples of Table 1 may at times fit more than one category, and are intended to be representative, not an exhaustive list. For example, the "Admission Type" may be applicable both to a present service data, but also to historical service data. Furthermore, present service data elements may be used as training data, for example, as a part of a test case to train an AI model to output an accurate prediction.

TABLE 1

Example User Data (which may be used to train an AI model or as input to a trained model)

| Example User Data Categories | Examples of User Data Elements per Category |
|---|---|
| Present Service/ Admission Data | Length of Stay (so far) Chief Complaint Code Admission Type Emergency Indicator Attending Authorized User Specialty Code Admitting Authorized User Specialty Code Procedure Service Line Code Procedure Severity, Laterality, Wound Codes |
| User Characteristics | User Height User Weight User BMI User Sex User Age Observation Status Registration Status Death Indicator |
| Historical Treatment Data | Previous 6 month Emergency Department (ED) Visit Count Previous 1 year ED Visit Count Previous 6 month Service Unit Visit Count Previous 1 year Service Unit Visit Count User Problem List (reported problems) Number of visits covered by insurance plan |

At 1012, the prediction system 902 generates a machine learning (ML) model 1014 based on the user data received at block 1006. As discussed above, although multiple ML models are illustrated herein, this is only for the purpose of illustration, and the computing environment can be enabled by a single ML model. Furthermore, any suitable artificial intelligence model may be used to enabled embodiments of the present disclosure. As used herein, the term "artificial intelligence" (AI) refers to any suitable computer-implemented artificial intelligence technique including machine learning (ML) (supervised or unsupervised), natural language processing, machine perception, computer vision, affective computing, statistical learning and classification (including use of hidden Markov models, Bayesian network models and Kalman filters), reinforcement learning including neural networks, search algorithms and optimization algorithms (including evolutionary computing) and automated reasoning.

As an example of an AI model that may be used to enable embodiments of the present disclosure, a distributed random forest (DRF) type of ML model may be employed. For example, multiple user data elements of the user data of Table 1 may be used to construct a forest of classification or regression trees (e.g., each tree pulling from a random subset of candidate features, each feature derived from one or more user data elements). The prediction system 902 may input training data from data store 226 (e.g., derived from the user data) into the untrained DRF. The training data may include suitable user data elements that correspond to the features chosen to construct the DRF. Furthermore, the user data elements may be curated in advance by an administrator and/or provider. For example, the administrator may know, for each user record, a "ground truth" data. The ground truth may correspond to the actual user outcome for a given service plan, after a certain period of time (e.g., 90 days). This ground truth data may be paired together with the training data elements as part of the curating process. The curation process may also further transform data elements that were received from the transformative processing engine 202 to be suitable for input to the DRF (e.g., converting user data elements into numerical values in an data array form that may be input into a classification or regression tree). Also, as indicated above, the training data may be retrieved from different sources, depending on the type of ML model being trained, which is further described in reference to FIG. 11. Here, in FIG. 10, the training data may be derived from user data drawn from multiple divisions (e.g., 1010(1)-1010(n)) across the enterprise. After inputting the training data into the untrained DRF model, the DRF model may be trained using well-known ML model training techniques (e.g., optimizing the number of decision trees, the maximum depth of a decision tree, the maximum number of features considered, etc.). In some examples, an ML model may be trained based on an error value, where the error value is based on a difference between the ground truth value (e.g., the user was ("1") or was not ("0") readmitted to a service unit within 90 days for service) and the predicted value (e.g., a probability of being readmitted within 90 days). In this example, the ML model may be trained to minimize the error value. Any suitable technique may be used to train an ML model used to implement embodiments of the present disclosure. A trained ML model may be further refined and improved, for example, by incorporating new features and/or different sets of training data. Once the ML model 1014 (e.g., DRF model) has been adequately trained, the ML model 1014 may be stored to the data store 226 (which may be associated with database 914 of FIG. 9).

At 1018, subsequent to training the ML model 1014, the prediction system 902 may retrieve user data. In an example, the user data may be retrieved from the data store 226 upon receiving input from a UC 1016. In one example, the input may be in the form of admission data 1017 that is input by the UC 1016 on the user device 1004, whereby the user device 1004 sends that data to the prediction system 902 over a network. The admission data 1017 may include any suitable information about a present admission of the user, including a user identifier (e.g., identification code, name, social security number, etc.), user admission time (corresponding to the time the user was admitted to a particular service facility of the enterprise), and other suitable information which may be used to identify the user and retrieve the user service record (UR). The UR may contain similar information as described in Table 1 above.

In another example, the admission data 1017 may be in the form of a configuration file input on the user device 1004 by the UC 1016 and sent to the prediction system 902 over the network. The configuration file may provide instructions to the prediction system 902 about when to automatically retrieve user data. For example, the instructions could configure the prediction system 902 to monitor for messages of a particular message format corresponding to user admission data, and retrieve a USR of the user from data store 226 whenever an HL7 message is received. The prediction system 902 may maintain a background process that continually checks a database (e.g., database 914) for new user admissions. In another example, the instruction could configure the prediction system 902 to retrieve user data on a predetermined schedule (e.g., multiple times per day), according to whatever users were admitted within a certain time interval. The background process could execute on a predetermined time interval to check for all new users that were admitted, or are still presently being serviced as admitted users. It should be understood that the prediction system 902 may be configured to generate a prediction at any suitable time. For example, the user may have already been admitted for service for an issue earlier in the day, and one or more service providers have updated the user's service record. The UC 1016 may wish to determine whether or not the user is likely to be readmitted for service within 90 days of eventual release, and thus determine if the user should receive a customized service plan (even while still receiving service in the service unit), to reduce the probability of readmission and increase user outcome quality. In other cases, prediction system 902 may receive data input from the user device of the UC 1016 to generate a prediction after the user has already been released, but before a predefined period (e.g., 90 days) has expired.

At 1020, the prediction system 902 may input user data (e.g., USR) into the ML model 1014. In an example, one or more data elements of the USR may be input into the trained ML model 1014. The data elements being input may correspond to whatever set of features are included in the trained ML model.

At 1022, the trained ML model 1014 generates a probability score. As discussed earlier, the probability score 1021 (e.g., a value between 0 and 1) may be a form of prediction. The prediction may correspond to whatever the trained ML model 1014 has been trained to predict. Continuing with an example above, the model 1014 may be trained to predict the probability that a user will be readmitted to a particular service facility of the service units of the enterprise within a predefined post-release time period (e.g., 90 days) that follows a date of release of the user from the present admission. Note that the ML model may be trained to predict other types of predictions. For example, the predefined post-release time period may be adjusted by the UC 1016, and the ML model be retrained accordingly. In another example, the ML model may be trained to predict the probability that the user will be readmitted within a certain time period, but analyzed with a different reported issue than the present reported issue. In some examples, the prediction 1021 may be stored to the data store 226 for later retrieval. This retrieval may include being used for presentation on the user device 1004, as discussed below. However, the retrieval may also be used, for example, to retrain the ML model 1014. For example, once a ground truth score is determined (e.g., whether or not the user actually was readmitted within a predefined period), the ground truth value may be compared against the predicted score to determine which types of user data inputs and/or trained ML models produced predictions with the largest errors, compared with the ground truth value.

At 1024, the prediction system 902 may provide the prediction for presentation. For example, the prediction system 902 may provide the probability score to the user device 1004 for presentation at the user device 1004. In some examples, the prediction may be retrieved by the prediction system 902 from the data store 226 prior to providing the probability score for presentation at the user device 1004. In some examples, as discussed above, the prediction system 902 may be configured to compute a prediction on a predetermined schedule (e.g., several times a day) up until the time a user is released from a service facility for the present admission. In some examples, the prediction may be provided by the prediction system 902 to the user device 1004 for presentation immediately upon being generated. In other examples, the prediction system 902 may provide a daily report including all the runs for that day. It should be understood that, although blocks 1018-1024 are described with reference to a single user, embodiments of the present disclosure should not be interpreted to be so limiting. For example, the prediction system 902 may receive as admission data a list of user identifiers for all presently admitted users throughout the enterprise (or division, or service facility). With this list, the prediction system 902 may retrieve all relevant USR's that correspond to the list, so that the prediction may be generated for each user presently admitted. It should be understood that any subset of users currently admitted may also be input (e.g., users above a certain age, users who have been admitted to for an ED or IP visit within the last six months or one year, etc.).

Figure 11:
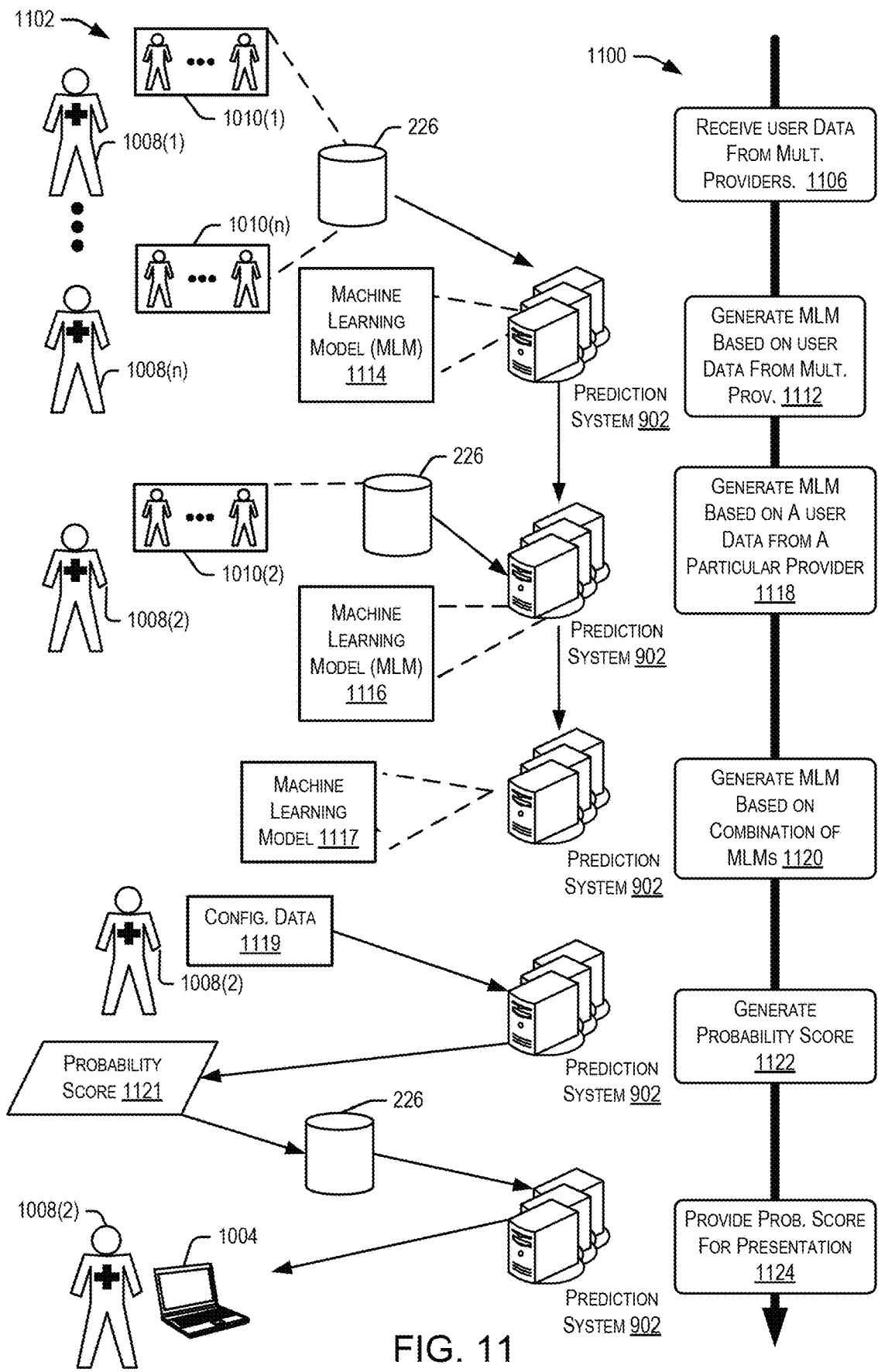
FIG. 11 is an example flowchart illustrating a process for providing a probability score that a user will be readmitted to a unit, according to at least one example.

FIG. 11 illustrates a simplified block diagram 1102 depicting an example process 1100, in accordance with at least one example. The process 1100 is an example process for generating a prediction using a trained ML model. The diagram 1102 depicts example states that correspond to the blocks of the process 1100. Whereas in FIG. 10, ML model 1014 is depicted as being trained utilizing training data drawn from user data 1010(1)-1010(n) across the enterprise, FIG. 11 depicts a layered approach that involves training multiple ML models 1114, 1116 (discussed further below). Although FIG. 11 depicts one example of utilizing a layered training approach, it should be understood that this is for illustration purposes only, and that any suitable layered training approach may be employed. The diagram 1102 includes the prediction system 902, the data store 226 of the transformative processing engine 202, and the user device 1004 that performs at least a portion of the process 1100.

The process 1100 begins at 1106 and may include receiving, by the prediction system 902, user data from multiple providers. Similar to FIG. 10 (block 1006), the training data may be input by multiple providers 1008(1)-1008(n) across the enterprise into each provider's respective user device, and transmitted over the network to the prediction system 902. Each provider may correspond to a representative for a particular service facility or division of the enterprise. The user data may be used to derive user training data. The training data may include similar data elements as described in reference to FIG. 10 and Table 1 above.

At 1112, the process 1100 includes generating, by the prediction system 902, a trained ML model 1114 based on the user data from multiple providers 1008(1)-1008(n) received at block 1106. The method used to generate the trained ML model 1114 may be similar to that described regarding block 1012 of FIG. 10.

At 1118, the process 1100 may include generating, by the prediction system 902, a trained ML model 1116 based on user data from a particular provider. The block 1118 may first include receiving, by the prediction system 902 from the data store 226, additional user data from a particular provider 1008(2) of the set of providers 1008(1)-1008(n). The information entered by the provider 1008(2) into the data store 226 may be in reference to the set of users 1010(2) that represent a portion of the plurality of service units of the enterprise (or division). In some examples, the user data received at block 1118 may be similar to that received at block 1112. However, in other cases, the user data may be curated in a way that is customized for the users 1010(2) of the particular service facility and/or division that is associated with provider 1008(2). For example, in the case of a particular service facility, an augmented set of user data elements may be stored in PDRs. For example, the particular service facility may have an atypically higher number of users with a certain characteristic (e.g., elderly users, or users in a certain socioeconomic range), and these characteristics may correspond to a more comprehensive set of user data elements than may be tracked by other service units. In any case, the user data for the particular service facility (or division) may also be stored to data store 226, similar to as described above. From this set of user data that represents only a portion (e.g., subset) of the plurality of service units, the block 1118 may next include generating another trained ML model 1116 that may be generated by the prediction system 902. It should be understood that the trained ML model 1116, being generated from user data of a portion of the service units (e.g., a single facility), may have different characteristics than the trained ML model 1114, being more tuned to the portion of service units. As discussed above, multiple ML models may be created, each representing a certain portion of the service units of the enterprise (e.g., single facility, division of units, or enterprise wide).

At 1120, the process 1100 may include generating, by the prediction system 902, an ML model 1117 that is based on a combination of ML models. In an example, the combination of models includes the earlier generated ML models 1114, 1116. The ML model 1117 may be a layered ML model that is layered in any suitable way. For example, the layered ML model 1117 may be generated by serializing the outputs of ML models 1114, 1116. The ML model 1114 may output a result, which may be fed as another data input to the ML model 1116, which in turn may output a final prediction. In another example, both ML models 1114 and 1116 may run in parallel and output a result. The results may be fed into a final prediction generator, which is preconfigured to weight the various outputs and output a final prediction result. It should be understood that one technical advantage of this design is that it may improve the accuracy of a prediction, especially in regards to large scale enterprises that may include multiple divisions, each division including multiple service units with different characteristics The accuracy may be improved by both reducing overfitting and underfitting of ML models caused by training data. By training a first ML model using training data drawn from multiple units, it helps to reduce overfitting, especially when a single facility may not have a large amount of training data (e.g., few users). On the other hand, by combining the first ML model with a second ML model that is more tailored to the data patterns of the particular service facility, underfitting may be reduced. Thus, a layered approach to utilizing ML models to produce a prediction may improve the overall accuracy of the prediction.

At 1122, the process 1100 may include generating, by the prediction system 902, a probability score. In an example, the prediction system 902 receives configuration data 1119 as input from a provider 1008(2). The configuration data 1119 may correspond to instructions for how the layered ML model 1117 should weight outputs from the different ML models 1114, 1116 when generating the probability score 1121. The configuration data 1119 may also correspond to a predetermined schedule for which the prediction system 902 should generate predictions 1121 for a set of users. As discussed above, the set of users 1010(2) may be a portion the total set of users of the enterprise. Similar to as described in FIG. 10, the probability score 1121 may be stored by the prediction system 902 to the data store 226 for future retrieval.

At 1124, similar to block 1024 of FIG. 10, the process 1100 includes providing, by the prediction system 902, the probability score 1121 for presentation. For example, the prediction system 902 may provide the probability score 1121 to the user device 1004 of the provider 1008(2). In some examples, the prediction system 902 accesses the probability score from the data store 226 prior to providing the probability score for presentation at the user device 1004.

FIG. 12 illustrates a graphical user interface (GUI) 1202 of a display 1200 of a user device. In some examples, the display 1200 may correspond to the display of user device 1004 of FIGS. 10 and 11. In FIG. 12, the GUI 1202 may correspond to a presentation of an application executing on the user device 1004. In an example, the application may be provided for a UC of the enterprise. The application may allow the UC to drill down to see predictions for users of a particular division 1204 (e.g., "West Florida Division") of the enterprise. The application may further allow the UC to drill down to see predictions for a particular service facility 1206 ("Oak Hill Medical Facility") of the division. The UC may be presented with a summary 1208 of notifications for particular users. For example, one notification may inform the UC that the prediction system 902 is scheduled to generate a batch of predictions at particular times. Another notification may alert the UC that a batch of predictions have already been generated and are awaiting the UC review in the Inbox.

The UC may further be able to filter results, using one or more filtering mechanisms 1210. For example, the UC may be able to select users of Oak Hill who fall under the Comprehensive Care for Joint Replacement (CJR) model. The CJR model is maintained by the CMS to help manage service for users undergoing hip and knee replacements. The CMS reimburses service providers for user services to users under a CJR model based on services rendered within an episode of service. As described earlier, this may include not only services rendered for acute service, but also post-acute service. Accordingly, the UC may want to determine which users may be at higher risk of readmission, so that the UC can prioritize coordinating service with service providers for the higher risk users.

Column 1212 of the GUI 1202 may present the UC with information related to the service being provided to users (e.g., schedule for service, assigned authorized user, last check-in time, etc.). Column 1214 may present the current location of the user in the service facility. Column 1216 may present the name of the user. Column 1218 may present the status of the particular user, and includes information such as the user admission time, user release time, the release code, the type of user (e.g., admitted user), etc. Column 1220 may present the risk of readmission for a particular user. For example, in the first row, user "Joe. D." has a 30% risk of being readmitted within 90 days of release for the current CJR intervention. In an example, the risk value presented may be the prediction scores 1021 or 1121 respectively described in reference to FIG. 10, 11. In other examples, the risk value provided in column 1220 may incorporate other factors in addition to the prediction (e.g., in FIG. 12, the prediction score may be presented as "Score: 0.<XX>," and the risk percentage may incorporate the value of the score). Column 1222 may represent certain service plan items for the particular user. For example, the user Joe D. may have several physical therapy appointments scheduled for post-acute service, based on the risk value of column 1220 for Joe D.

Figure 13:
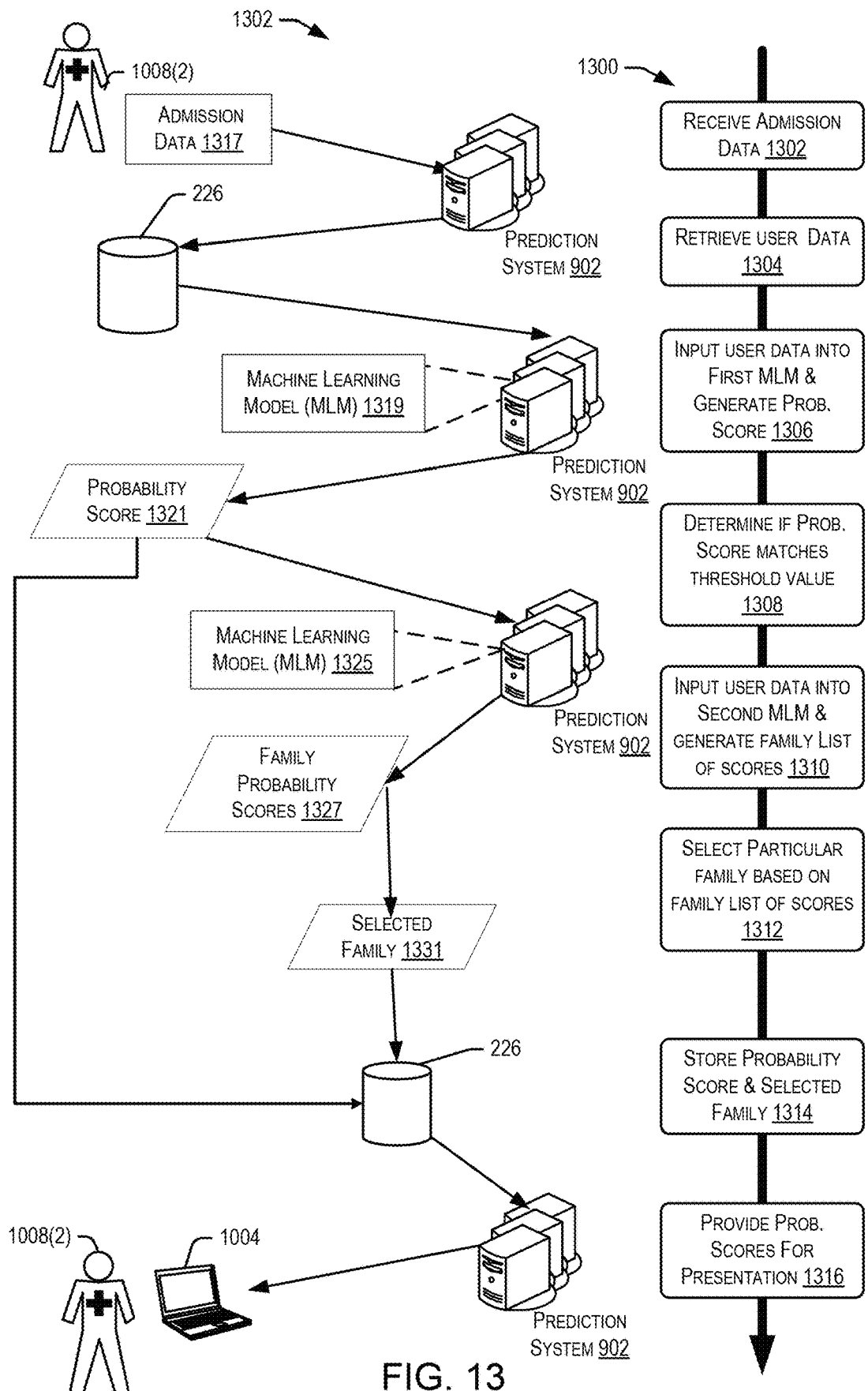
FIG. 13 is an example flowchart illustrating a process for providing a probability score that a user will be readmitted to a unit, according to at least one example.

FIG. 13 illustrates a simplified block diagram 1302 depicting an example process 1300, in accordance with at least one example. In FIG. 13, the process 1300 involves generating a prediction that is targeting a different context. Specifically, the prediction is directed towards predicting whether a user analysis result (and corresponding service) will be classified as belonging to any one service group of a set of qualifying service groups. If so, then the process further produces a prediction that corresponds to predicting a particular service group identification of the set of qualifying service groups.

At 1302, the prediction system 902 may receive admission data. As discussed in reference to block 1018 of FIG. 10, the admission data 1317 may be received through different mechanisms. In one mechanism, the admission data 1317 may be received as directly as input from the user device of the provider (e.g., UC) 1008(2). In another mechanism, the admission data 1317 may be in the form of a configuration file (e.g., or executable code) containing instructions that sets up an automated process for retrieving user data without manual user input.

At 1304, based on the admission data 1317, the prediction system 902 retrieves user data. The user data may be in the form of a USR from the data store 226. As discussed above, this USR may include characteristics of the user, historical service data, and present service data. It should be understood that in some examples, the admission data 1317 may correspond to a list of admission data 1317, the list corresponding to a plurality of users (e.g., within a single service facility, or spread across multiple units). For simplicity, the example discussed below focuses on the admission data for a single user.

At 1306, similar to block 1020 of FIG. 10, the prediction system 902 may input user data into a first ML model 1319 and generate a probability score 1321. The user data may include one or more data elements of the USR. The data elements being input may correspond to whatever set of features were used to train the first ML model 1319. The first ML model 1319 may correspond to a binomial classification model (BCM) that is trained to determine a probability whether an input (e.g., the user) falls inside or outside of a set (e.g., set of service groups). The BCM may be implemented using any suitable form of AI model (e.g., a DRF), as described above. In this example, the prediction 1321 may correspond to a probability score that the user analysis result/service (e.g., service group identification) will be classified as belonging to any one service group of a set of qualifying service groups. The set of qualifying service groups (discussed further below in reference FIG. 14) may be specific to a service facility (or set of service units of a division), and may be predetermined by the UC or other service facility administrator 1008(2) and input to the prediction system 902 to train the first ML model 1319 and/or train the second ML model 1325, discussed below.

At block 1308, the prediction system 902 determines if the probability score 1321 matches a threshold value. The threshold value may be specific to a service facility (or set of service units of a division), and may be predetermined by the UC or other service facility administrator 1008(2). As discussed in examples herein, a prediction "matching" the threshold value may include scenarios where the prediction value is greater than or equal to the threshold value. It may also include scenarios where the prediction value is strictly greater than the threshold value. In either case, the threshold value corresponds to a trigger (and filtering) mechanism (e.g., a floor) that determines whether the prediction system 902 will further process the user to generate a prediction corresponding to a particular service group prediction. If the prediction matches the threshold value, then the prediction system 902 proceeds to the next block. If not, the process may terminate. Whether or not a match occurs, the prediction 1321 may be stored to the data store 226 for further processing (e.g., to be used to assist in training ML model improvements, and/or to be presented on the user device 1004).

At 1310, upon determining a match, the prediction system 902 may input user data into a second trained ML model 1325 and generate a family list (e.g., of service group probability scores). The user data may include one or more data elements of the USR of the user. In an example, the one or more data elements may be the same as those input at block 1306 into first ML model 1319. In another example, the one or more data elements may be different (or partially overlap) than those input at block 1306. Furthermore, the second ML model 1325 may be trained using different features and parameters than first ML model 1319. For example, while first ML model 1319 may be a BCM, second ML model 1325 may be a multi-category classification model (MCCM). For example, the second ML model 1325 may output a list of predictions (e.g., service group probability scores 1327), whereby each service group probability score respectively corresponds to a service group of the set of qualifying service groups that was discussed at block 1308.

At 1312, the prediction system 902 may select a particular service group based on the family list of probability scores. In an example, the prediction system 902 may select from the list of qualifying service groups based on a respectively sorted list of family probability scores 1327. For example, the prediction system 902 may select the family probability score with the highest probability in the list 1327.

At 1314, the prediction system 902 may store the probability score and the selected family. For example, the prediction system 902 may store the probability score 1321 and the selected family 1331. In some examples, the prediction system 902 may also store the full list of family probability scores 1327 to the data store 226, which may be later presented to the UC 1008(2) for further review. It should be understood that the prediction 1321 may be stored to the data store 226 at block 1308 or block 1314 of the process 1300. In some examples, the prediction 1321 and/or selected family 1331 may not be stored to a data store 226, and thus block 1314 may be bypassed.

At block 1316, the prediction system 902 provides one or more of the predictions 1321, 1327, 1331 for presentation. This presentation may be done in a similar fashion as described previously with respect to block 1024 of FIG. 10.

Figure 14:
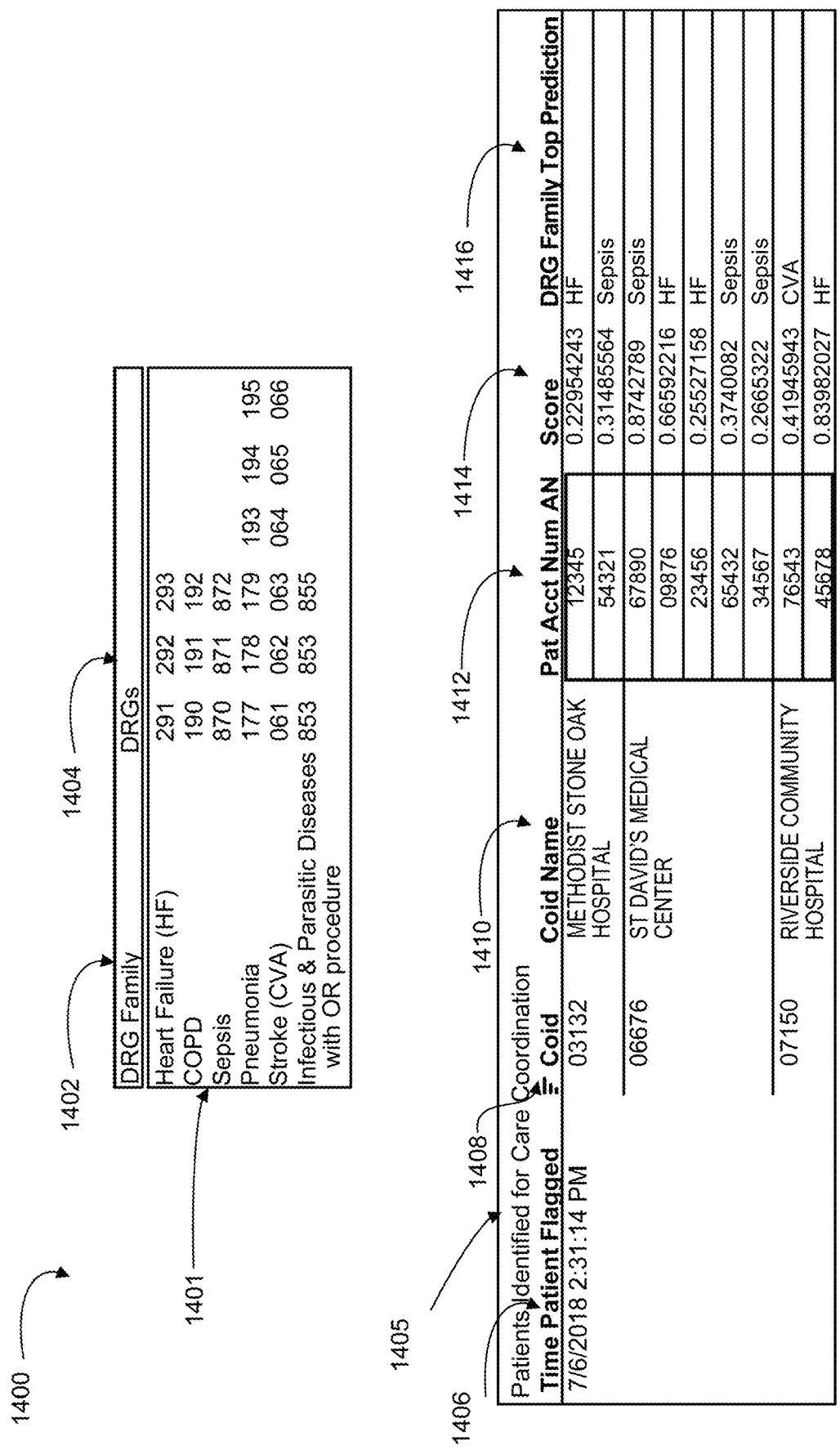
FIG. 14 is an example diagram illustrating a GUI for providing a probability score that a user will be readmitted to a unit, according to at least one example.

FIG. 14 illustrates a graphical user interface (GUI) of a display 1400 of a user device. In some examples, the display 1400 may correspond to the display of the user device 1004 of FIG. 13. GUI 1401 illustrates an example table corresponding to set of qualifying service groups, which may be presented by an application executing on the user device 1004. In some examples, the table may be stored in the data store 226, and the composition of the set may be adjusted by the UC 1008(2) via the GUI 1401. As described at block 1308 of FIG. 13, the set of qualifying service groups may be used to configure/train an ML model (e.g., ML model 1319, ML model 1325). Column 1402 illustrates example service groups, whereby each service group may include one or more service group codes that are listed under column 1404. For example, the "Heart Failure (HF)" service group may include service group codes 291, 292, and 293. These codes may also correspond to service group codes maintained by the CMS and used to determine whether a user qualifies for a bundled payment model, as described earlier. In some examples, the service group codes may be used for any suitable classification purpose (e.g., determining if a user should qualify for a particular type of service coordination).

Meanwhile, the configuration illustrated in the GUI 1401 may be used by one of the ML models to generate output (e.g., block 1316 of FIG. 13) that is presented on a GUI 1405 of the display of user device 1004. In the example illustrated by GUI 1405, the prediction system 902 may perform a batch run over multiple service units (each facility containing multiple admitted users) on a predetermined schedule. Column 1406 may represent the time the batch run was performed. In some examples, the batch run may be performed multiple times per day, to ensure that the UC 1008(2) is kept up to date with the latest user status. Column 1408 may correspond with an identification code (coid) for a service facility, and column 1410 may correspond with the service facility name. Column 1412 may correspond with an account number for a particular user that is admitted to the service facility. Finally, column 1414 may correspond to the prediction 1321 output at block 1306 of FIG. 13, while column 1416 may correspond to the selected service group 1331 selected at block 1312 of FIG. 13. In this example, each selected service group in column 1416 may correspond to one of the service groups of the set of qualifying service groups in column 1402 represented in GUI 1401. In the example illustrated in GUI 1405, each of the service units (e.g., Methodist Stone Oak, St. David's, etc.) may be associated with the same configuration (e.g., within the same division). For example, each service facility 1410 may be associated with the same set of qualifying service groups 1402, and accordingly may be associated with the same trained ML models 1319, 1325. The service units 1410 may also have the same threshold value that is applied to prediction score 1414 (e.g., at block 1308).

Figure 15:
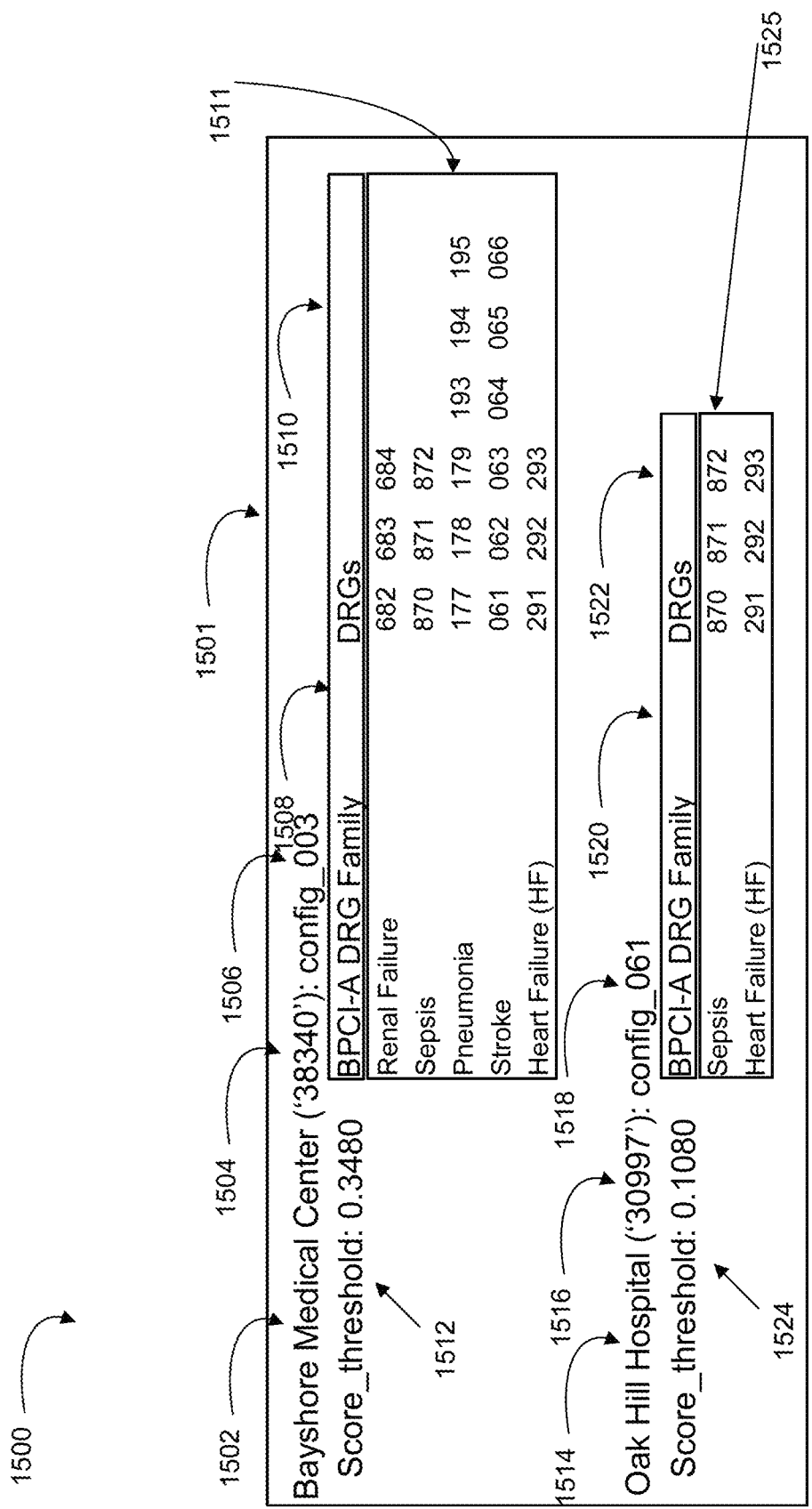
FIG. 15 is an example diagram illustrating a GUI for providing a probability score that a user will be readmitted to a unit, according to at least one example.

FIG. 15 illustrates a GUI 1501 of a display 1500 of a user device, which may correspond to user device 1004. Similar to FIG. 14, GUI 1501 illustrates example tables, each corresponding to a set of qualifying service groups, which may be presented by an application executing on the user device 1004. However, in contrast to FIG. 14, FIG. 15 illustrates an example whereby different service units may each be associated with different configurations, thus producing different ML models per service facility.

As an example, GUI 1501 allows a UC to view configurations for multiple service units in the enterprise. A first table 1511 may be associated with a first service facility 1502 ("Bayshore"), which may have an identification value (e.g., coid) 1504 of '38340.' Bayshore may be associated with a configuration ID 1506 (e.g., "config_003"), the configuration ID being associated with a particular configuration that is used to train an ML model associated with the facility (e.g. ML models 1319, 1325). It should be understood that multiple service units may also be associated with the same configuration, as described in reference to FIG. 14.

Config_003 1506 may define a first plurality of qualifying service groups, as shown in column 1508, along with the corresponding service group codes represented in column 1510. Additionally, config_003 1506 may also specify a first threshold value 1512 (e.g., corresponding to the threshold value described in reference to block 1308 of FIG. 13).

Meanwhile, a second table 1525 may be associated with a second service facility 1514 ("Oak Hill"), which may have an identification value 1516 of '30997.' Oak Hill may be associated with a configuration ID 1518 (e.g., "config_061"). Config_061 1518 may define a second set of qualifying service groups, as shown in column 1520, along with the corresponding service group codes represented in column 1522. Additionally, config_061 1518 may also specify a threshold value 1524. For additional context, each service facility may be associated with a unique set qualifying service groups, for example, according to the service facility's particular enrollment in a bundled payment model with CMS (e.g., Bundled Payments for Care Improvement (BPCI) or BPCI-Advanced (BPCI-A)). In some embodiments, the unique set of qualifying service groups associated with one facility may be entirely disjoint from the unique set associated with another facility. However, in other embodiments, for example, as illustrated in FIG. 15, the sets may overlap (e.g., both containing Heart Failure (HF) and Sepsis). Moreover, each service facility may determine a threshold value that is designed to achieve an acceptable capture rate and error rate that corresponds to per-facility key performance indicator (KPI) goals, described further below in reference to FIGS. 17 and 18.

To further illustrate how a first ML model that is trained for a first facility may be different than a second ML model trained for a second facility, consider the example depicted in FIG. 15. In this example, both units may utilize common user data as training data to train their respective ML models. However, the training data used to train each model may be labeled differently. For example, the first facility (e.g., Bayshore 1502) may label users that qualify for a service group within the first set 1508 as having a "positive" outcome, whereas, users that don't qualify for a service group within the first set 1508 may be labeled as having a "negative" outcome. Conversely, the second facility (e.g., Oak Hill 1514) may label users that qualify for a service group within the second set 1520 as having a "positive" outcome, whereas, users that don't qualify for a service group within the second set 1520 may be labeled as having a "negative" outcome. In this way, units (and/or divisions) may share common user data used for training, and yet the respective training data may be labeled differently, resulting in differently configured ML models per facility.

FIG. 16 illustrates a GUI 1601 of a display 1600 of a user device (e.g., user device 1004), whereby the GUI 1601 represents a dashboard presentation for a UC (e.g., a UC covering the enterprise or a division of the enterprise). The dashboard presentation 1601 is presented as an output of a process that is similar to process 1300 of FIG. 13. In FIG. 16, the dashboard 1601 may be generated based on the combined output of the process 1300 being repeated across multiple units and/or configurations, and compiled together in a uniform view to present the dashboard presentation 1601.

Turning to the dashboard 1601, column 1612 may correspond to the admission date and time that the user was admitted to the service unit. Column 1614 may represent the time the batch run was performed. Similar to as described in reference to GUI 1405, in some examples, the batch run may be performed multiple times (e.g., three times) per day, to ensure that the UC is kept up to date with the latest user status. Column 1616 may correspond with an identification code of the service facility, and column 1618 may correspond with the service facility name. Column 1620 may correspond with an account number for a particular user that is admitted to the service facility. Column 1622 may correspond to the prediction 1321 (e.g., probability score) output at block 1306 of FIG. 13, while column 1624 may correspond to the selected service group 1331 selected at block 1312 of FIG. 13.

In contrast to GUI 1405 of FIG. 14, and referencing FIG. 15, dashboard 1601 is presented by drawing from prediction data that is generated utilizing different configurations. For example, although Bayshore (COID=38340) and Oak Hill (COID=30997) are respectively associated with different configurations (e.g., Bayshore being associated with config_003 1506, Oak Hill being associated with config_061 1518), user scores from both service units are presented in a uniform fashion in the dashboard 1601. Thus, Bayshore may list "KidneyUrinaryT1" as being the DRG Family Top Prediction in column 1624, which may correspond to "Renal Failure" under column 1508 of FIG. 15. Also, Oak Hill may list "HeartFailShock" as being the DRG Family Top Prediction in column 1624, which may correspond to "Heart Failure (HF)" under column 1520 of FIG. 15. Furthermore, although each service center may output a probability score under column 1622, the threshold value (which qualifies each probability score to be further processed) varies between service units. For example, in the case of Oak Hill, the threshold 1524 is 0.1080, and therefore a score of 0.292 matches the threshold. The same score of 0.292 would not have matched the threshold 1512 for Bayshore, which is 0.3480, and thus may have resulted in a termination of the process 1300 at block 1308 of FIG. 13.

Figure 17:
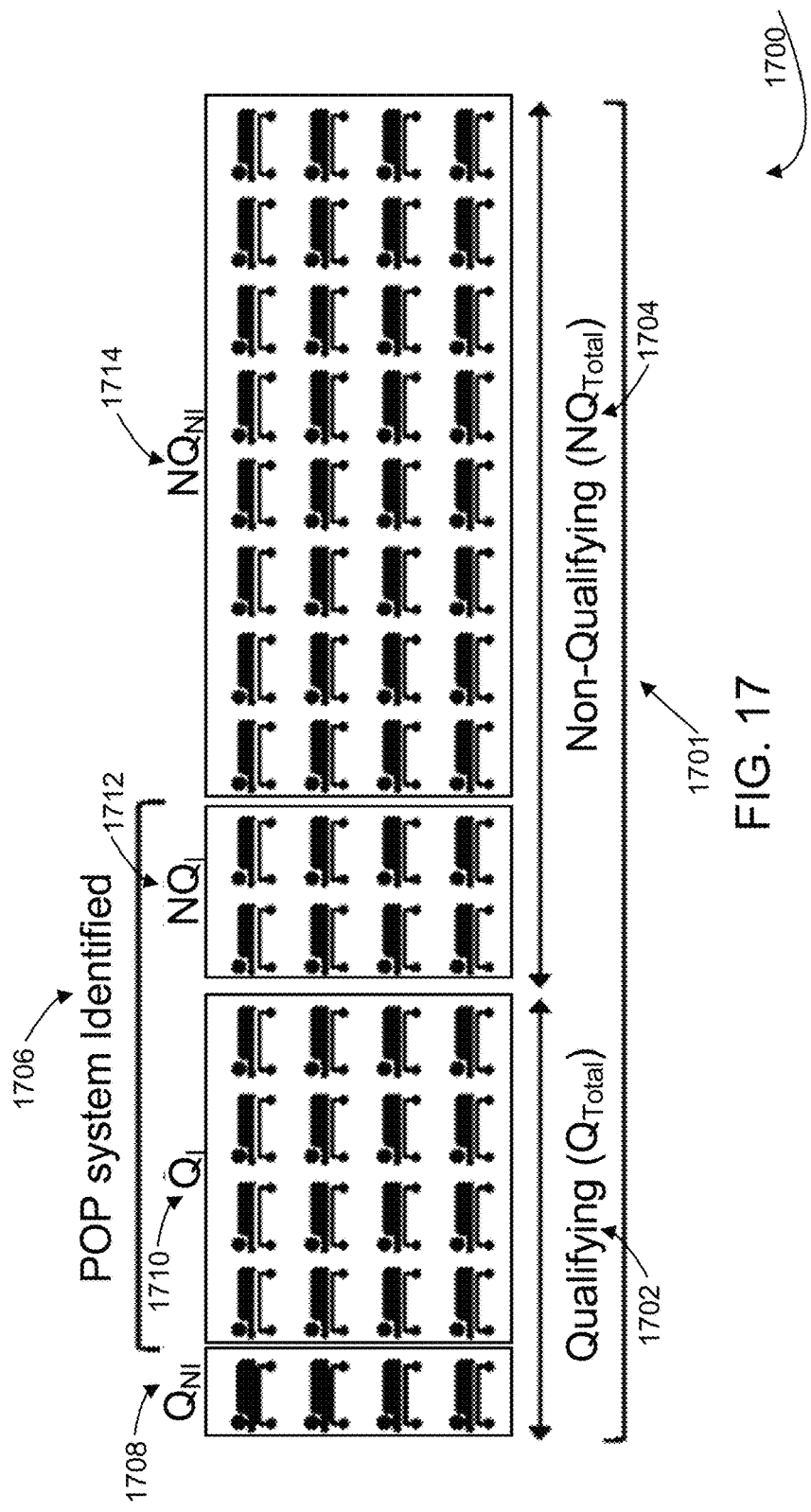
FIG. 17 is an example diagram illustrating metrics for providing a probability score that a user will be readmitted to a unit.

FIG. 17 illustrates a representation 1700 of KPI metrics which may be tracked by the prediction system, and which may be used by a UC of a service facility to gauge system performance and set an appropriate threshold value. Users included within bracket 1701 may represent a collection of admitted users of a service facility which already have a service group code associated with their analysis result. For example, it is known whether or not a given user qualifies to be part of a bundled payment model (also known as a "bundle"), and as such, the ground truth is known. As described above, examples of a bundled payment model include the Bundled Payments for Care Improvement (BPCI) or BPCI-Advanced (BPCI-A)) programs of CMS. Users included within set 1702 represent users who qualify to be part of a bundle (e.g., Bundle Qualifying User Population ($Q_{Total}$)). Users included within set 1704 represent users who do not qualify to be part of a bundle (e.g., Non-Qualifying User Population ($NQ_{Total}$)). Both sets 1702 and 1704 correspond to actual ground truth metrics.

Turning to metrics that correspond to predictions generated by the prediction system 902, users included within set 1708 represent users who are qualified to be in a bundle, but were not identified (e.g., missed) by the prediction system 902 ($Q_{Not\ Identified\ (NI)}$), which may be referred to as "Under Captured." Users included within set 1706 represent users whom the prediction system 902 identified as being qualified to be within a bundle (whether or not that prediction actually corresponds to the ground truth ($Q_{Total}$)) (which may be referred to as "Prediction System Identified User Population"). Within set 1706, users identified within set 1710 are users who were identified as being qualified to be in a bundle and who actually do qualify ($Q_I$, which may be referred to as "Captured"). Also within set 1706, users identified within set 1712 are users who were identified as being qualified to be in a bundle, but who actually do not qualify ($NQ_I$, which may be referred to as "Over Captured"). Finally, users identified by set 1714 are users who were not identified as being qualified to be in a bundle, and who truly are not-qualified to be in a bundle ($NQ_{NI}$).

With these metrics, several derivative metrics may be identified. First, a capture rate may represent the fraction of the bundle-qualifying users that are identified by the prediction system (i.e., Capture Rate=Captured/Bundle Qualifying User Population=$Q_I/(Q_{NI}+Q_I)$). Second, a false discovery rate may represent the fraction of prediction system user identifications that were incorrect (i.e., False Discovery Rate=Over Captured/Prediction System Identified User Population=$NQ_I/(Q_I+NQ_I)$). Third, a false positive rate may represent the fraction of non-qualifying users identified by the prediction system (i.e., False Positive Rate=Over Captured/Non-Qualifying User Population=$NQ_I/(NQ_I+NQ_{NI})$). An ideal goal of the prediction system is for the capture rate to be as close to 100% as possible, while also minimizing the false discovery rate and the false positive rate. One way to adjust each of these rates is to adjust the threshold value, which will have the effect of increasing or decreasing the number of users identified by the prediction system as being part of a bundle (e.g., see block 1308 of FIG. 13). As such, and for example, decreasing a threshold value may increase the capture rate, but may also have the effect of increasing the false discovery rate and/or the false positive rate. A service facility UC may determine what is a desired capture rate, and what are tolerable false discovery and/or false positive rates. The tolerable false discovery and/or false positive rates, either individually or collectively, may be referred to herein as an "acceptable capture error rate." Based on the determination of a desired capture rate and an acceptable capture error rate, the UC may set a threshold value to meet those target goals, as described further in reference to FIG. 18, below.

Figure 18:
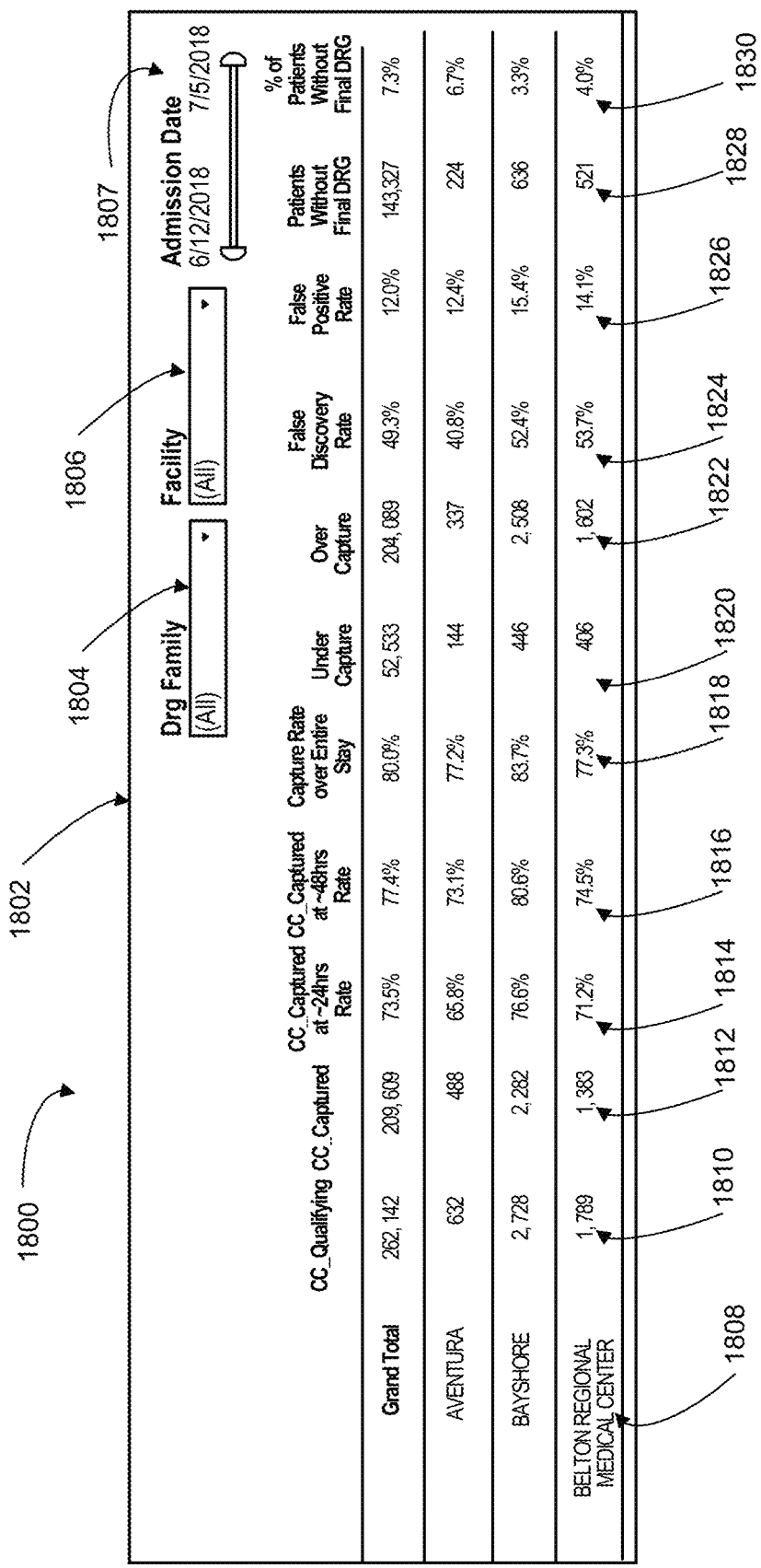
FIG. 18 is an example diagram illustrating a GUI for providing a probability score that a user will be readmitted to a unit, according to at least one example.

FIG. 18 illustrates a GUI presentation 1802 on a display 1800 of a user device 1004 of a UC, which may be used to assist the UC in determining the quality of prediction data being generated by the prediction system. The GUI presentation 1802 may also assist the UC in determining if and how to adjust a threshold value for a particular service facility to achieve the desired KPI goals for that facility. The example presentation illustrated by GUI 1802 shows a dashboard of capture statistics, per service facility, for a user service coordination (SC) program managed by the UC. The UC may be able to filter information using one or more filters. For example, the UC may filter by service group 1804 or by facility 1806. The UC may also be able to view metrics within a selected range of admission dates 1807.

Turning to the table presented in GUI 1802, and referencing the metrics identified in reference to FIG. 17, the first row of the table may correspond to a "Grand Total" that summarizes the statistics captured across all service units in the filtered view. In the example of FIG. 18, the numbers are only illustrative-only a subset of individual service units are shown, and therefore the Grand Total values may not reflect the sum of the metrics for the service units presented. Column 1808 may correspond with an identification of a service facility (e.g., "Bayshore"). Column 1810 may correspond to a number of users per service facility that were actually qualifying for coordinated service (e.g., $Q_{Total}$). Column 1812 may correspond to a number of qualifying users that were captured by the prediction system for that facility (e.g., $Q_I$). Column 1814 may correspond to a capture rate (e.g., $Q_I/(Q_{NI}+Q_I)$) for the first twenty-four hours of admission to the service facility. Column 1816 may correspond to a capture rate for the first forty-eight hours of admission to the service facility. Column 1818 may correspond to an overall capture rate for the selected time period 1807. In an example, Bayshore's overall capture rate 1818 may be represented by dividing column 1812 by column 1810 (i.e., 2,282/2,728=83.7%). Column 1820 may correspond to a number of users that were under-captured (e.g., $Q_{NI}$) for the selected time period 1807. Column 1822 may correspond to a number of users that were over captured for the selected time period 1807 (e.g., $NQ_I$). Column 1824 may correspond to the false discovery rate ($NQ_I/(Q_I+NQ_I)$=2,508/(2,282+2,508)=52.4%). Column 1826 may correspond to the false positive rate ($NQ_I/(NQ_I+NQ_{NI})$) (calculation not shown). Column 1828 may correspond to the number of users who do not yet have a final service group assigned to them, and therefore a ground truth value (e.g., whether the user qualifies for a coordinated service program) is not yet determined. Column 1830 may correspond to a percentage of the users within the selected time period 1807 who do not have a final service group assigned.

Continuing with the Bayshore example, a UC of the Bayshore may analyze the table presented in GUI 1802 to determine whether to adjust the currently configured threshold value (e.g., threshold value 1512 of FIG. 15, currently set to be 0.3480). The UC may determine that they seek to have a capture rate of at least 80%, and are willing to tolerate a false discovery rate of 50%. First, the UC determines that the short-term capture rate for the first twenty-four hours of admission to the service facility is 76.6% (column 1814), and the capture rate for the first forty-eight hours of admission to the service facility is 80.6% (column 1816). Moreover, the long-term average capture rate is 83.7% (column 1820). Accordingly, the UC is satisfied with the capture rate. The UC further determines that the false discovery rate is 52.4% (column 1824), which is slightly higher than desired. However, the UC determines that for Bayshore's KPI goals, a higher capture rate is a higher priority than reducing the false discovery rate. As such, the UC determines to not adjust the threshold value 1512. It should be understood that, in some circumstances, in order to achieve both the target capture rate and a target false discovery rate, a ML model may need to be retrained, for example, as discussed in FIGS. 10 & 11.

Figure 19:
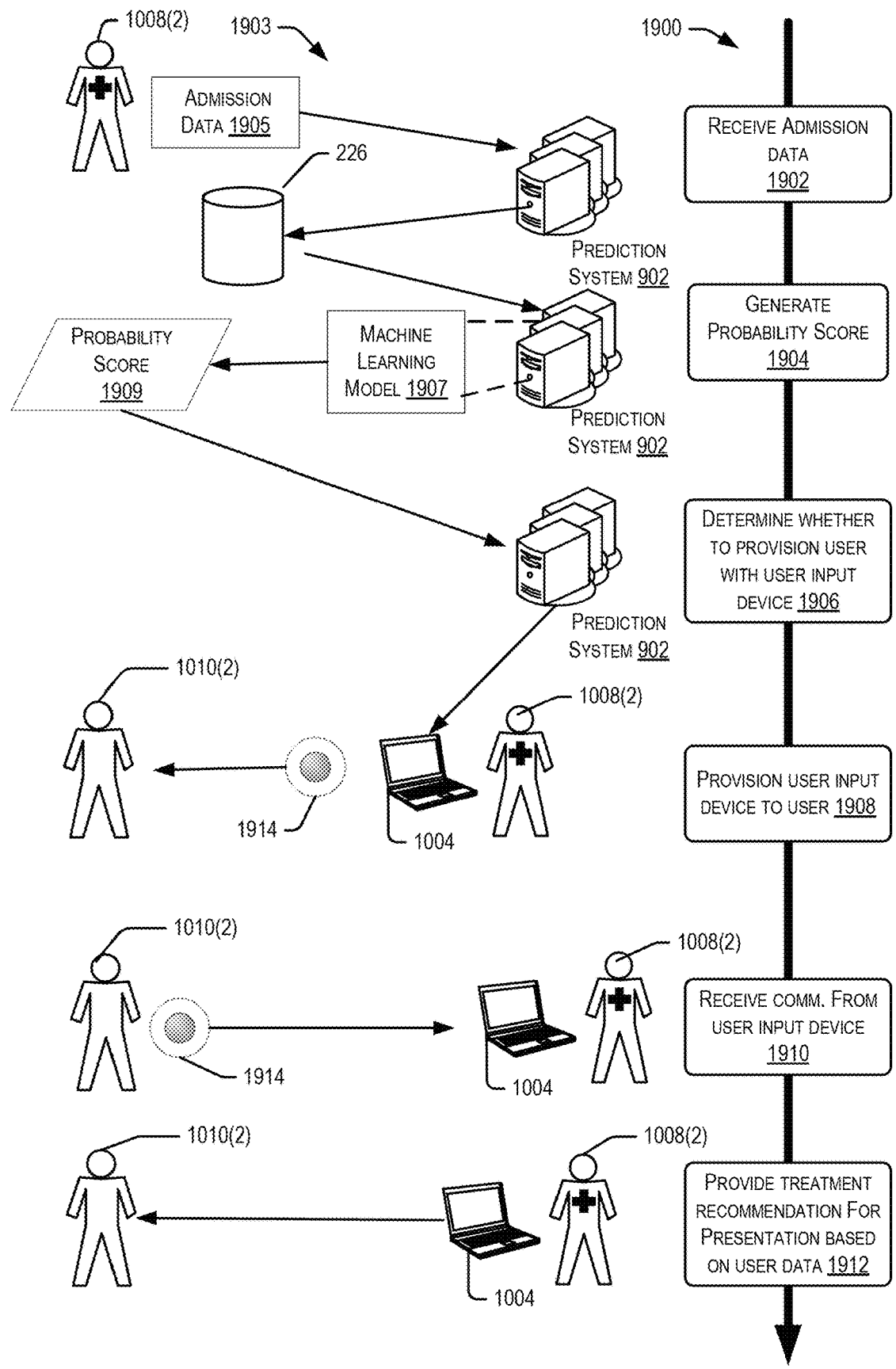
FIG. 19 is an example and flowchart illustrating a process for providing a probability score that a user will be readmitted to a unit, according to at least one example.

FIG. 19 illustrates a simplified block diagram 1903 depicting an example process 1900, in accordance with at least one example. The diagram 1903 includes the prediction system 902, the data store 226 of the transformative processing engine 202, the user device 1004 that performs at least a portion of the process 1900, and a user input device 1914 for further use in coordinating service for the user.

At 1902, the prediction system 902 may receive admission data 1905. As discussed earlier (e.g., at block 1018 of FIG. 10), the admission data 1317 may be received through different mechanisms. In one mechanism, the admission data 1317 may be received directly as input from the user device of the provider (e.g., UC) 1008(2). In another mechanism, the admission data 1317 may be in the form of a configuration file (e.g., or executable code) containing instructions that sets up an automated process for retrieving user data without manual user input. For simplicity, the example discussed below focuses on the admission data for a single user.

At 1904, the prediction system 902 may generate a probability score 1909. To generate the probability score 1909, the prediction system 902 may first, based on the user admission data 1905 received at block 1902, retrieve a USR from the data store 226. Next the prediction system 902 may input one or more data elements of the USR into a trained ML model 1907.

In one example, the ML model 1907 of the prediction system 902 may include a plurality of sub-ML models. The sub-ML models may correspond to one or more of the previous ML models discussed, for example, in reference to FIGS. 10 and 13. For example, a first sub-ML model may be similar to the trained ML model 1014 of FIG. 10. The first sub-ML model may generate a first probability score that the user will be readmitted to one of the plurality of associated service units of the enterprise within a predefined post-release time period that follows a date of release of the user from a present admission. A second sub-ML model may be similar to the trained ML model 1319 of FIG. 13. The second sub-ML model may generate a second probability score that the service group identification of the user will match one of a plurality of qualifying service groups at the time the user is released from the present admission. The ML model 1907 may combine the first prediction and the second prediction into a final probability score. In one example, the ML model 1907 may combine the probability scores by computing the product of the two scores. For example, the final probability score may correspond to the probability that a user will be readmitted within a predefined post-release period and will also qualify to be part of a bundled payment model. This final score may be useful to a UC because it alerts the UC, not only that the user may be at a high risk of being readmitted, which would increase the overall resources needed to service the user, but also that the service facility may only receive a payment for a single episode of service for the user's service. Accordingly, the UC is thereby put on notice that the user may be a good candidate for coordinated service, which may help the UC to prioritize service among users. It should be understood that any suitable combination of predictions that are generated from different ML models may be sufficient to perform embodiments of the present disclosure.

Continuing with block 1904, based on the one or more data elements of the USR into the trained ML model 1907, the trained model 1907 may output the probability score 1909 (e.g., a final probability score based on the combination of outputs from sub-ML models, discussed above).

At 1906, the prediction system 902 may determine whether to provision the user with the user input device 1914. The prediction system 902 may perform this determination by determining if the probability score 1909 matches a threshold value. As discussed earlier, the threshold value may be used as trigger mechanism to determine whether the UC 1008(2) should provision the user 1010(2) of the service facility with the user input device 1914, discussed further below. In some examples, this threshold value may be used to identify users at high risk of readmission and/or probability of being included within a bundled payment model. For these types of users, it may be useful to provide the user with an easy way to contact the UC 1008(2) and receive prompt recommendations for service. If the prediction 1909 matches 1911 the threshold value, the prediction system 902 may transmit an alert message to a user device 1004 of the UC 1008(2) with an instruction to assign the user input device 1914 to the user 1010(2).

At 1908, based on the determination by the prediction system 902 (at block 1906), a user input device to be provisioned to the user 1010(2). In an example, the provisioning may involve associating the user input device 1914 with the particular user 1010(2). For example, when the user is released from the present admission, an identifier of the user input device 1914 (e.g., a QR code on the device 1914) is scanned. A user identifier may also be scanned or otherwise accessed (e.g., from a user armband or from the USR). A user phone number may also be obtained from the user or the USR. This phone number may be associated with a user input device identifier of the user input device 1914 and the user identifier in a user input device record. This user input device record may be stored in the data store 226 (e.g., along with the USR). The user input device record may be shared with a service recommendation system (not shown) managed by the UC 1008(2). The user input device 1914 may be any suitable device, including a hardware and/or software implementation. In an example, and as described below in reference to FIG. 20, the device 1914 may be a physical button that is configured such that, when a user pushes the button, a signal is sent over a network (e.g., cellular network, wired network, or any suitable network) to a user device 1004 of the UC 1008(2). In another example, the device 1914 may represent a software application on a mobile phone that is configured to send a text message to the UC upon the press of a soft button displayed in the application. In yet another example, the device 1914 may represent an Amazon Echo (or similar) device that is configured to receive voice input from the user, and automatically in turn send a message to the UC.

At 1910, the user device of the UC receives a communication from the user input device 1914. For example, at some time post-release, the user device 1004 of the UC 1008(2) may receive a message sent from the user input device 1914 upon a press of a button by the user 1010(2). In one example, when the user pushes a button (or any other suitable communication means, as described above), a signal is sent over a network and received by the user device 1004. The device may first be received by a routing and/or processing system (e.g., service recommendation system (not shown)), and routed to the user device 1004. Upon receiving the message from the user input device 1914, the processing system may first retrieve a set of data from the data store 226 that corresponds to service providers associated with the user 1010(2), as well as user data from the USR, and/or the user input device record. This user data may correspond to a current service plan of the user, as well as previous diagnoses associated ongoing service issues of the user (e.g., cancer services, hip replacement therapy, heart valve maintenance, etc.). In this way, the processing system may provide to the UC 1008(2) a unified list of service plan data for various diagnoses, and the corresponding service providers for each step of the service plan. In some examples, when the user pushes the button, the message sent to the processing system may include information such as the user's current location and other service providers nearby to the user (e.g., a nearby pharmacy), which may assist the UC 1008(2) to better coordinate options for the user receiving service.

At 1912, the user device of the UC provides service recommendations for presentation based on the user data. In an example, upon the user device 1004 receiving a unified list of service recommendations (e.g., based on the data compiled at block 1910 by the service recommendation system), the user device 1004 may present these recommendations on a display of the user device 1004 for the UC 1008(2) to analyze and provide service recommendations to the user 1010(2). It should be understood that some service recommendations may take various forms, beyond direct contact with the user. For example, the recommendations may include contacting a local pharmacy to get a refill for medication, scheduling a follow-up appointment to be seen by an authorized user or other service provider, or even contacting an emergency service provider to contact the user immediately. Some of these follow up actions/recommendations may be performed automatically by a processing system associated with the user device 1004. For example, depending on the user's service history, the processing system may automatically contact an emergency service technician upon receiving a message from the push of the button of the user input device 1914. In this way, the prediction system 902 (in coordination with other systems) may improve user service coordination and thus improve service efficiencies.

Figure 20:
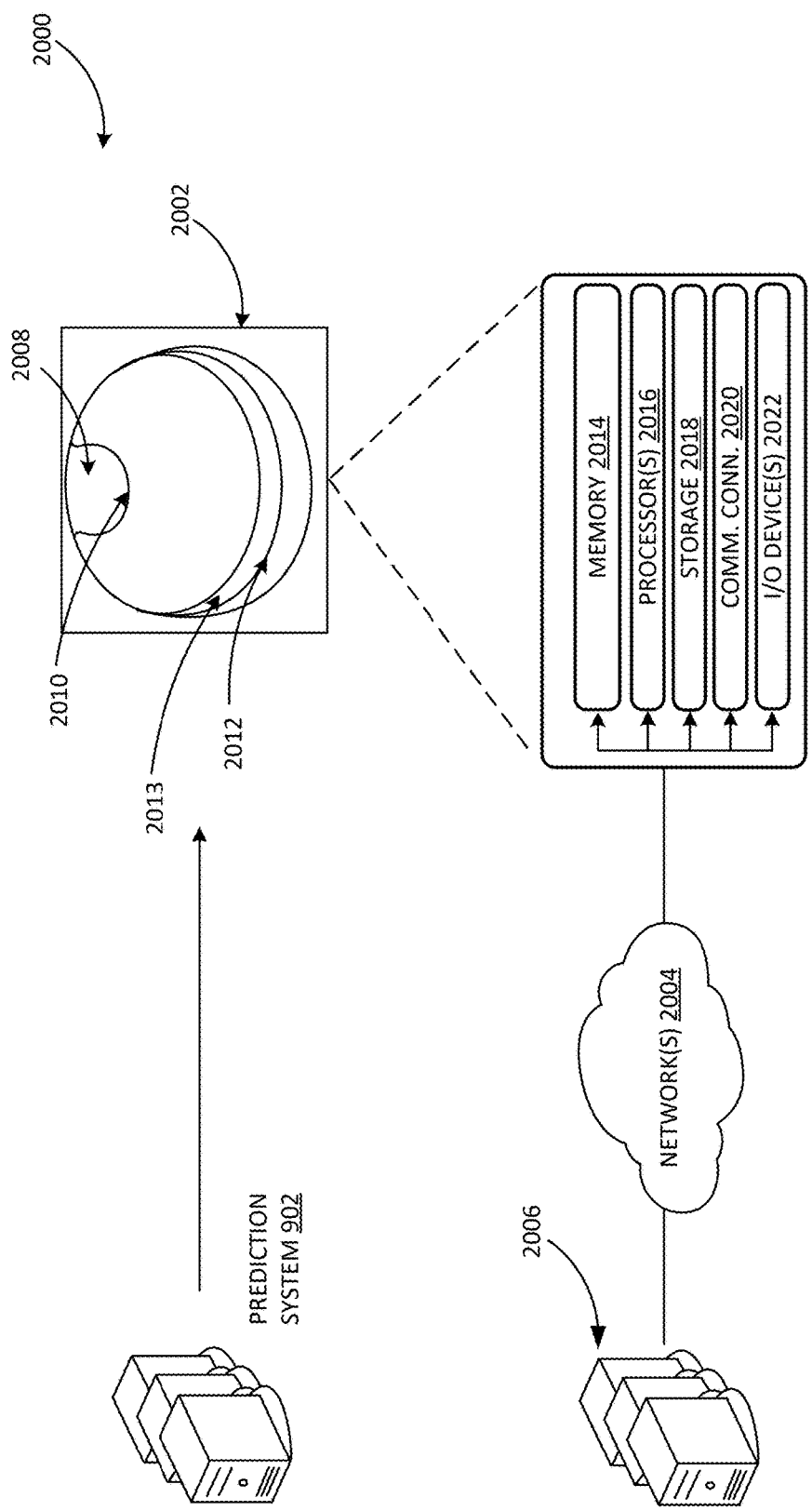
FIG. 20 is an example architecture illustrating an input device that is provisioned to a user based on a probability that a user will be readmitted to a unit, according to at least one example.

FIG. 20 illustrates a simplified block diagram 2000 of an example architecture for a user input device that is provisioned to a user based on output from a prediction system. The provisioned user input device may then be used to contact a UC of the enterprise. In an example, the user input device 2002 (which may correspond to user input device 1914 of FIG. 19) may be a hardware device received by a user (e.g., user 1010(2)) upon the determination by prediction system 902 that the user is at a high risk of being readmitted and will likely qualify for a bundled payment model. The process of provisioning the user input device 2002 to the user may be similar to as described in FIG. 19. Once provisioned, the user input device 2002 may be communicatively coupled to a computer system 2006 (e.g., the service recommendation system described in FIG. 19) via a network 2004. The network 2004 may include any suitable communication path or channel such as, for instance, a wire or cable, fiber optics, a telephone line, a cellular link, a radio frequency (RF) link, a WAN or LAN network, the Internet, or any other suitable medium. The network 2004 may include any one or a combination of many different types of networks, such as cable networks, the Internet, wireless networks, cellular networks, and other private and/or public networks. Once provisioned, upon the press of a button of the user input device 2002, a message may be sent over the network 2004 and received by the service recommendation system 2006 (e.g., block 1910), which may in turn process the message and provide service recommendations for the user to be presented on the user device 1004 of the UC 1008(2). It should be understood that the service recommendation system 2006 and the prediction system 902 may also be connected (e.g., via network 2004), and/or coupled via hardware to operate as a single system.

Turning to user input device 2002 in greater detail, as described above, the user input device 2002 may be a hardware device as shown in FIG. 20. In an example, the user input device 2002 may include a body 2012, which may be in the form of a plastic substrate, housing, or other structure. The user input device 2002 may also include a light-emitting diode (LED) that is connected to the body 2012 and visible by the user. The user input device 2002 may also include a button 2008 that may be pressed by the user. In some examples, the user input device 2002 may also include a speaker and/or microphone 2013. The user input device 2002 may be powered by a battery (not shown) that is housed within the body 2012 (e.g., alkaline battery, lithium battery), and may be turned on/off using any suitable method (e.g., pressing and holding the button 2008 for several seconds). Any suitable method may be used to power the user input device 2002.

Turning to the system components of the user input device 2002 in more detail, the user input device 2002 may include a memory 2014, one or more processing units (or processor(s)) 2016, a storage unit 2018, a communication device 2020, and an I/O device 2022. The processor(s) 2016 may be implemented as appropriate in hardware, computer-executable instructions, firmware or combinations thereof. Computer-executable instruction or firmware implementations of the processor(s) 2016 may include computer-executable or machine executable instructions written in any suitable programming language to perform the various functions described. The memory 2014 may store program instructions that are loadable and executable on the processor(s) 2016, as well as data generated during the execution of these programs. Depending on the configuration and type of user input device 2002, the memory 2014 may be volatile (such as random access memory (RAM)) and/or non-volatile (such as read-only memory (ROM), flash memory, etc.). In some implementations, the memory 2014 may include multiple different types of memory, such as static random access memory (SRAM), dynamic random access memory (DRAM) or ROM. The user input device 2002 may also optionally include additional storage 2018, such as either removable storage or non-removable storage including, but not limited to, magnetic storage, optical disks, and/or tape storage. The disk drives and their associated computer-readable media may provide non-volatile storage of computer-readable instructions, data structures, program modules, and other data for the computing devices. The user input device 2002 may also contain communications connection(s) 2020 that allow the user input device 2002 to communicate with a stored database, another computing device or server (e.g., service recommendation system 2006), user terminals, and/or other devices over the network(s) 2004. The communications connection(s) 2020 may be in the form of a contactless element interface, for example, an antenna configured to send/receive wireless signals, including cellular signals (e.g., GSM (Global System for Mobile Communications)) or other wireless signals (e.g., NFC (Near Field Communication), BLE (Bluetooth Low Energy), RFID (Radio Frequency Identifier)). The user input device 2002 may also include input/output (I/O) device(s) and/or ports 2022, such as for enabling connection with a keyboard, a mouse, a pen, a voice input device (e.g., microphone 2013), a touch input device, a display, speakers (e.g., speaker 2013), a printer, etc.

Turning to the contents of the memory 2014 in more detail, the memory 2014 may include an operating system and one or more application programs or services for implementing the features disclosed herein. For example, the memory 2014 may comprised code, which, in conjunction with the processor 2016, configure the user input device 2002 to transmit (e.g., broadcast) a message containing a user input device identifier (e.g. a serial number of the device, MAC address, firmware version, etc.) The memory 2014 may also comprise code that is configured to receive a message containing provisioning information. In an example, the provisioning information may contain a user identifier, a user telephone number, a UC telephone number, a list of data codes, etc. The user input device 2002 may store this provisioning information to the user input device 2002 (e.g., in memory 2014 or storage 2018). The memory 2014 may further comprise code that is configured to transmit a message (e.g., over a cellular network using GSM protocol) upon receiving the press of the button 2008. In an example, the message may be transmitted to a destination based on the provisioning information that was previously received (e.g., UC telephone number). In another example, depending on the way in which the button was pressed, a particular data code may be transmitted within the message to the destination. For example, if the user quickly presses the button three times in a row, the user input device 2002 may send a message with a data code indicating that the user has an emergency and requires urgent attention. The memory 2014 may further comprise code that is configured to activate the LED 2010 on the user input device 2002 upon sending a message. For example, the light 2010 may start flashing once the message is being transmitted. Once the user input device 2002 receives an acknowledgment message indicating that the message has been received (e.g., an acknowledgment according to GSM protocol), the user input device 2002 may cause the LED to output a solid (i.e., non-flashing) light. In another example, the user input device 2002 may cause the color to change (e.g., from red to green). In this way, the user may receive confirmation that the message has been received. As described earlier in reference to FIG. 19 (e.g., block 1910-1912), once the message sent by the user input device 2002 has been received by the user device 1004, appropriate action may be taken to coordinate service for the user. Furthermore, as described earlier, although the embodiment of FIG. 20 includes a hardware device, the features described herein in reference to FIG. 20 may also be implemented in other forms (e.g., a software application with a software button on a mobile phone, a voice interaction device that is configured to transmit a message upon receiving a human voice input, etc.).

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:
1. A prediction system, comprising:
at least one memory comprising computer-executable instructions; and
one or more processors in communication with the memory and configured to access the memory and execute the computer-executable instructions to, at least:
train a first machine learning model based at least in part on data elements of a first set of user profiles of a first plurality of users from multiple providers, the first set of user profiles including data associated with characteristics of the first plurality of users and admissions of the first plurality of users;
train a second machine learning model based at least in part on data elements of a second set of user profiles of a second plurality of users from a particular provider, the second set of user profiles including data associated with characteristics of the second plurality of users and admissions of the second plurality of users;

generate a layered machine learning model that is based on a combination of the first machine learning model and the second machine learning model;

receive, over a network, admission data comprising a user identifier and a user admission time, the user admission time corresponding to a time a user was admitted to a unit to receive service for a particular admission;

retrieve, based at least in part on the user identifier, a user profile of the user from a data store of the prediction system, the user profile including data associated with at least one of (I) characteristics of the user, (II) the particular admission, or (III) previous admissions of the user;

input a data element of the user profile into the layered machine learning model of the prediction system, the layered machine learning model configured to input the data element of the user profile into the first machine learning model and the second machine learning model and weigh respective outputs by the first machine learning model and the second machine learning model indicating a likelihood that the user will be readmitted to the unit within a particular time period that follows a release from service for the particular admission and generate therefrom a score indicating the likelihood that the user will be readmitted to the unit within the particular time period that follows the release from service for the particular admission, wherein the at least one memory stores configuration data that instructs the prediction system how to weight each of the respective outputs when generating the score;

output, by the layered machine learning model of the prediction system and based at least in part on the data element, the score indicating the likelihood that the user will be readmitted to the unit within the particular time period that follows the release from service for the particular admission; and provide the score corresponding to the unit to a user device of a user coordinator of the unit for subsequent presentation on the user device, the user coordinator coordinating one or more service providers of the unit, the score provided to the user device over the network.

2. The prediction system of claim 1, wherein the memory comprises further computer-executable instructions that, when executed by the one or more processors, further cause the prediction system to, at least:

enroll the user for receiving coordinated service based at least in part on determining that the score matches a threshold value.

3. The prediction system of claim 1, retraining at least one of the first machine learning model and the second machine learning model based on the data element of the user profile, the score, and a ground truth score corresponding to whether or not the user was actually readmitted within the particular time period.

4. The prediction system of claim 1, wherein the unit is one of a plurality of associated units, and wherein the memory comprises further computer-executable instructions that, when executed by the one or more processors, further cause the prediction system to, at least:

train at least one of the first machine learning model and the second machine learning model based at least in part on user profiles of users of the plurality of associated units.

5. The prediction system of claim 1, wherein the score is a first score and the likelihood is a first likelihood, and wherein the memory comprises further computer-executable instructions that, when executed by the one or more processors, further cause the prediction system to, at least:

determine, based at least in part on a second data element of the user profile, a second score indicating a second likelihood that the user will be classified into a particular service group of a plurality of service groups, a service group of the plurality of service groups comprising one or more service group codes, a service group code corresponding to a particular analysis result or issue associated with the user, and provide the second score to the user device of the user coordinator, wherein the second score is used to determine whether service for the user qualifies to be classified under a particular payment model.

6. The prediction system of claim 5, wherein the memory comprises further computer-executable instructions that, when executed by the one or more processors, further cause the prediction system to, at least:

determine a third score based at least in part on the second score and the first score; and determine, based at least in part on the third score, that the user should be assigned to receive coordinated service.

7. The prediction system of claim 1, wherein the memory comprises further computer-executable instructions that, when executed by the one or more processors, further cause the prediction system to, at least:

determine that the score matches a threshold value;

determine an instruction to assign the user an input device based at least in part on the score matching the threshold value, wherein the input device is configured to transmit a signal to the prediction system upon receiving a press of a button of the input device, the press of the button corresponding to a request by the user for service assistance;

receive the signal indicating that the button of the input device has been pressed; and provide potential service recommendations for the user for presentation on the user device of the user coordinator.

* * * * *